(12) United States Patent
Kanda et al.

(10) Patent No.: US 9,176,037 B2
(45) Date of Patent: Nov. 3, 2015

(54) SPECIMEN PROCESSING SYSTEM

(75) Inventors: Katsuhiro Kanda, Hitachinaka (JP);
Makoto Nogami, Tsuchiura (JP); Izumi Waki, Tokyo (JP)

(73) Assignee: HITACHI HIGH-TECHNOLOGIES CORPORATION, Tokyo (JP)

( * ) Notice: Subject to any disclaimer, the term of this patent is extended or adjusted under 35 U.S.C. 154(b) by 103 days.

(21) Appl. No.: 13/387,229

(22) PCT Filed: Aug. 10, 2010

(86) PCT No.: PCT/JP2010/063536
§ 371 (c)(1),
(2), (4) Date: Feb. 15, 2012

(87) PCT Pub. No.: WO2011/019032
PCT Pub. Date: Feb. 17, 2011

(65) Prior Publication Data
US 2012/0134895 A1    May 31, 2012

(30) Foreign Application Priority Data

Aug. 10, 2009  (JP) .................................. 2009-186001

(51) Int. Cl.
*B01L 99/00*       (2010.01)
*G01N 1/40*        (2006.01)
(Continued)

(52) U.S. Cl.
CPC .............. *G01N 1/4055* (2013.01); *G01N 1/405* (2013.01); *G01N 35/025* (2013.01); *G01N 2035/00485* (2013.01); *G01N 2035/00544* (2013.01); *G01N 2035/0455* (2013.01); *G01N 2035/1058* (2013.01)

(58) Field of Classification Search
None
See application file for complete search history.

(56) References Cited

U.S. PATENT DOCUMENTS 4,186,187 A * 1/1980 Jahnsen et al. .................. 422/64
5,556,598 A    9/1996 Raybuck et al.
(Continued)

FOREIGN PATENT DOCUMENTS

CN    1349428 A    5/2002
EP    607 442 A1   7/1994
(Continued)

OTHER PUBLICATIONS

T. Annesley et al, "Simple Extraction Protocol for Analysis of Immunosuppressant Drugs in Whole Blood", Clinical Chemistry, 2004, vol. 50, pp. 1845-1848.
(Continued)

*Primary Examiner* — Jill Warden
*Assistant Examiner* — Benjamin Whatley
(74) *Attorney, Agent, or Firm* — Mattingly & Malur, PC

(57) ABSTRACT

Disclosed is a specimen processing system that includes means 91 circularly disposed to carry a reaction vessel 2 used for separating and extracting desired substances from a specimen to be processed, a plurality of processing steps, executed as processing progresses along a transport line for the reaction vessel 2 on the transport means 91, for conducting various processes upon the specimen to be processed that is accommodated in the reaction vessel 2, suctioning and discharging means 94 that dispenses the specimen from a specimen container 1 supplied to the system, into the reaction vessel 2, and a filtering vessel section 2b provided as a part of the reaction vessel 2. This system configuration allows realization of a rapid preprocessing system capable of reducing the number of disposable parts of a low carry-over type, suppressing a decrease in cost performance, operating with high collection efficiency, and employing compact devices.

9 Claims, 17 Drawing Sheets

(51) Int. Cl.
*G01N 35/02* (2006.01)
*G01N 35/04* (2006.01)
*G01N 35/00* (2006.01)
*G01N 35/10* (2006.01)

(56) References Cited

U.S. PATENT DOCUMENTS

| | | | |
|---|---|---|---|
| 5,585,068 A * | 12/1996 | Panetz et al. | 422/64 |
| 5,660,727 A * | 8/1997 | Gleave et al. | 210/141 |
| 2002/0123156 A1 | 9/2002 | Tajima | |
| 2008/0064115 A1 | 3/2008 | Hiramatsu et al. | |

FOREIGN PATENT DOCUMENTS

| | | |
|---|---|---|
| GB | 2 232 599 A | 12/1990 |
| JP | 63-118665 A | 5/1988 |
| JP | 3-170046 A | 7/1991 |
| JP | 4-106472 A | 4/1992 |
| JP | 5-99936 A | 4/1993 |
| JP | 06-018532 A | 1/1994 |
| JP | 6-289031 A | 10/1994 |
| JP | 6-315603 A | 11/1994 |
| JP | 8-320274 A | 12/1996 |
| JP | 10-267936 A | 10/1998 |
| JP | 2000-105248 A | 4/2000 |
| JP | 2000-235037 A | 8/2000 |
| JP | 2003-121317 A | 4/2003 |
| JP | 2006-007081 A | 1/2006 |
| JP | 2006-317330 A | 11/2006 |
| WO | WO02/086488 A1 | 10/2002 |

OTHER PUBLICATIONS

Japanese Office Action received in Japanese Application No. 2011-526765 dated Apr. 30, 2014.

* cited by examiner

FIG. 10

| STEP | POSI-TION | SECTION THAT OPERATES | OPERATION |
|---|---|---|---|
| 1 | 306a | REACTION VESSEL MOUTING/COLLECTING MECHANISM 320 | SETS REACTION VESSEL 2 (FILTERING SECTION 2b AND SOLID-PHASE EXTRACTION SECTION 2c) ON TURNTABLE 91. |
| 2 | 307a | DISPENSING MECHANISM 340 | SUPPLIES METHANOL OR LIKE AS ORGANIC SOLVENT TO REACTION VESSEL 2 (FOR CONDITIONING CHARACTERISTICS OF SOLID-PHASE EXTRACTION FILLER 420). |
| 3 | 308a | PRESSURIZING MECHANISM 52E | CONDITIONS CHARACTERISTICS OF SOLID-PHASE EXTRACTION FILLER 420 BY SENDING ORGANIC SOLVENT BY PRESSURIZING. |
| 4 | 309a | DISPENSING MECHANISM 340 | SUPPLIES WATER TO REACTION VESSEL 2 (FOR CONDITIONING CHARACTERISTICS OF SOLID-PHASE EXTRACTION FILLER 420). |
| 5 | 310a | PRESSURIZING MECHANISM 52F | CONDITIONS CHARACTERISTICS OF SOLID-PHASE EXTRACTION FILLER 420 BY SENDING WATER BY PRESSURIZING. |
| 6 | 311a | DISPENSING/MIXING MECHANISM 94 | DISPENSES WHOLE-BLOOD SPECIMEN INTO REACTION VESSEL 2. |
| 7 | 311a | 1ST REAGENT (HEMOLYZING SOLUTION) DISPENSING MECHANISM 323. | DISPENSES HEMOLYZING SOLUTION AND INTERNAL STANDARD SOLUTION INTO REACTION VESSEL 2. |
| 8 | 311a | DISPENSING/MIXING MECHANISM 94 | CONDUCTS MIXING. |
| 9 | 311a | 2ND REAGENT (PROTEIN-PRECIPITATING SOKUTION) DISPENSING MECHANISM 333 | DISPENSES PROTEIN-PRECIPITATING SOLUTION INTO REACTION VESSEL 2. |
| 10 | 311a | DISPENSING/MIXING MECHANISM 94 | CONDUCTS MIXING. |
| 11 | 301a | PRESSURIZING MECHANISM AND FILTERING SECTION REMOVAL MECHANISM 52B | APPLIES FILTERING PRESSURE AND REMOVES FILTERING SECTION 2b. |
| 12 | 302a | DISPENSING MECHANISM 340 | SUPPLIES WATER OR LIKE AS WASHING LIQUID TO SOLID-PHASE EXTRACTION SECTION 2c. |
| 13 | 303a | PRESSURIZING MECHANISM 52C | APPLIES PRESSURE TO WASH SOLID-PHASE EXTRACTION FILLER 420. |
| 14 | 304a | DISPENSING MECHANISM 340 | SUPPLIES METHANOL OR LIKE AS ELUTING SOLUTION TO SOLID-PHASE EXTRACTION SECTON 2c. |
| 15 | 305a | PRESSURIZING MECHANISM 52D | APPLIES PRESSURE TO ELUTE ANALYTES FROM SOLID-PHASE EXTRACTION FILLER 420. |
| 16 | (306a) | SPECIMEN INTRODUCING MECHANISM 350 | INTRODUCES EXTRACT WITHIN EXTRACT CUP 2d INTO ANALYZER'S ION SOURCE 430. |
| 17 | 306a | REACTION VESSEL MOUNTING/COLLECTING MECHANISM 320 | COLLECTS AND DISCARDS SOLID-PHASE EXTRACTION SECTION 2c. |

SPECIMEN PROCESSING SYSTEM

TECHNICAL FIELD

The present invention relates to a specimen processing system that rapidly and efficiently preprocesses a biological specimen or a specimen of water, soil, food, or the like. The preprocessing of the specimen is intended for separation/purification, extraction, and filtering of target constituents contained in the specimen, including the mixing of the specimen and a reagent solution.

BACKGROUND ART

Various techniques exist for the separation and extraction of target constituents from a specimen of a mixture of various constituent. The techniques are such that utilizes the physical properties derived from the molecular sizes, molecular weights, molecular shapes of the desired constituents, or biochemical properties such as solubility or affinity. For example, separation technology such as chromatography has been widely developed for the extraction of trace constituents contained in blood or other biological specimens. Development of separation techniques and optimization of methods using appropriate separation columns, solid-phase extraction packing sorbents, magnetic beads, etc., according to the target constituents, has been achieved. In addition, the volumes of specimens useable for preprocessing tend to become increasingly smaller, and in such tendency, a higher yield and more accurate separation/extraction are demanded. In accordance with these progress and advancement of separation/extraction techniques, a more efficient preprocessing system, that can meet the increase in the number of kinds of reaction solutions and steps used for separation/extraction, and is capable of separating/extracting target constituents from smaller quantities of specimens, is demanded.

The immunosuppressant drugs administered to organ transplant recipients, for example, tend to have high lipid-solubility and high partition ratio into blood cells. Therefore, upon measuring the concentration of an administered immunosuppressant drug in blood, it is necessary to preprocess by hemolyzing whole blood and removing the internal contents of the blood cells, and then extracting the drug adsorbed onto proteins or the like.

In general, hemolyzing can be executed by applying chemical, physical, or biological mechanisms. For example, hemolysis can be chemically caused by using various solvents or surface-active agents and thereby dissolving or damaging the lipids that constitute cell membranes. Applicable physical methods include pressurizing, centrifuging, mixing, freezing and thawing, hypotonizing (hypotensioning), and so on. Useable biological methods include forming transmembrane protein complexes by means of antibody binding or complement binding to the blood cells, forming holes/pores in the blood cell membranes using the hemolysins produced by pathogenic bacteria, and more.

Particularly, blood cell bursting by hypotonization is simple in principle. It is a method that ruptures cell membranes by reducing the salt concentration of blood with H2O (or the like) to reduce osmotic pressure around the blood cells, and thus causing excessive uptake of water into the blood cells. Normal saline solutions generally have a concentration equivalent to 0.90% NaCl, and it is known to cause hemolysis if diluted to a concentration equivalent to 0.50%-0.35% NaCl.

In addition, γ (gamma)-globulin and other key proteins present in large quantities in blood can be condensed and precipitated by applying the chelating effect of zinc. For this purpose, a method of conducting protein removal simultaneously with hemolyzing by adding a zinc sulfate solution, instead of H2O, to the blood is commonly used as an alternative method, which is also used for ZTT (Zinc sulfate Turbidity Testing) as well.

Another alternative method for collecting the desired constituents adsorbed onto the proteins in blood is deproteinization. Deproteinization is a process in which an organic solvent is added to a hemolyzed specimen to denature proteins and to extract desired constituents into the organic solvent. Centrifuging is generally provided to separate condensed proteins and a supernatant, and then to collect the supernatant. The deproteinization process is performed to condense and remove the proteins included in diverse forms and large volumes in blood. Conducting such process allows specimens derived from whole blood to be processed in the same manner as serum or plasma specimens.

As discussed above, organic solvents also yield a hemolytic effect. Therefore, hemolyzation and deproteinization may be conducted by adding an organic solvent to blood directly. Further, in order to complement the deproteinization effect in such cases, the foregoing method adding zinc sulfate may also be applied.

Performing the above-described process to a whole-blood specimen allows drugs with high blood cell partition ratio to be collected in a solution state. The specimen can then be subjected to purifying operations such as solid-phase extraction or liquid chromatographic separation. Typically, a supernatant collected after deproteinization is then dried up, and is redissolved in a solution of an appropriate volume so as to reduce the amount of liquid and to concentrate target constituents. After this, the redissolved solution is subjected to, for example, liquid chromatography-mass spectrometry (LCMS) or the like, whereby the concentrated target constituents are separated/purified and detected for subsequent identification and quantitative analysis.

The specimens from which the target constituents are separated and extracted using any one of those techniques are usually composed of various substances and constituents exhibiting different properties. To extract the desired trace constituents efficiently, the specimens need to undergo preprocessing such as specimen preparation and pre-purification to achieve an extractable state. Two basic technical elements used in common for such preprocessing are, a technique of dispensing solution and mixing the specimen with a reaction solution or the like by mixing, and a filtering technique. One technical problem associated with dispensing and mixing is carry-over problem during the preprocessing, where during continuous preprocessing of a plurality of specimens to be assayed for target substances of low concentrations, the trace quantities of constituents contained in one preprocessed specimen are left as a contaminant in the dispensing/mixing mechanisms or filtering mechanism of the preprocessing apparatus after the preprocessing of that specimen. This carry-over during the preprocessing of one specimen will reduce the accuracy of separation/extraction of the next specimen. This can be prevented by thoroughly cleaning the internal parts of the apparatus after the preprocessing of the previous specimen. Another method to prevent this problem is removing, for each specimen, parts that are likely to remain contaminated such as the dispensing pipettes, mixing parts, filtering parts, and others, and replacing these parts with exchangeable ones (hereinafter, called disposable parts). The other method is integrating these parts or using parts of common specifications to reduce the number of disposable parts.

Non-Patent Document 1 describes examples of preprocessing and separation/extraction techniques for specimens, the techniques required in measuring the concentration of an immunosuppressant drug in whole blood by means of liquid chromatography-mass spectrometry. According to Non-Patent Document 1, preprocessing and separation/extraction processes conducted prior to the measurement of liquid chromatography-mass spectrometry include:

(a) Hemolyzation (blood dissolving) by adding pure water or the like to whole blood, (b) protein precipitation by adding zinc sulfate and/or methanol after the hemolyzation, (c) centrifugation for removing the precipitated proteins, and (d) solid-phase extraction of the supernatant cleared of the precipitated proteins, to further remove impurities likely to interfere with liquid chromatography-mass spectrometry.

As a method for removing protein sediments that do not use centrifugation, a method is also known where the solution is forcibly passed through a filter and the protein sediments stuck to the filter is removed. However, although individual apparatuses dedicated for the steps of preprocessing methods (a), (b), (c), (d) are generally well known, there is no apparatus that has fully automated steps (a) to (d).

For example, if the protein sediments in step (b) remain to be further processed, impurities will be redissolved from the sediments during the washing and eluting phases of solid-phase extraction step (d). The impurities will significantly deteriorate the accuracy of subsequent mass spectrometric measurement. It is therefore necessary to remove the sediments in step (c).

The operations spanning these steps are difficult to automate, and thus, these operations have traditionally been performed with manual operation. This has increased the number of containers/vessels and implements used for temporary collection of the solution between steps and for the dispensing operations in the next steps. Additionally, due to trace constituents sticking to these containers/vessels and implements, a carry-over as well as a loss in the collection, reduction in total analytical sensitivity and accuracy are caused, and therefore obstructing the analyzable volumes of specimens to become smaller.

Patent Document 1 relates to an example of a batch-processing type of solid-phase extraction technique as preprocessing for separating and extracting target constituents from specimens to be processed. In this conventional technique, a solid-phase extraction plate is formed with 96 solid-phase extraction columns for accommodating the specimens and is mounted in an upper vacuum rack, which is set on a horizontally and vertically movable mechanism. The upper vacuum rack is pressed against a lower vacuum rack, and each specimen is suctioned from the lower vacuum rack by a vacuum pump. Consequently, the target constituents are adsorbed onto a filter provided in each solid-phase extraction column, and the target constituents adsorbed onto the filter are eluted and extracted. Patent Document 1 also discloses that a low-carryover type disposable pipette/nozzle tip is used to dispense the specimen. Further, a method of mixing by suctioning/discharging solution with the disposable pipette/nozzle tip to achieve low-carryover mixing is disclosed.

The automated solid-phase extraction process according to Patent Document 1 is of a batch-processing type, so that efficient preprocessing is possible when the number of specimens to be preprocessed and assayed is an integral multiple of the number of specimens (96), which the solid-phase extraction plate can retain. The number of specimens to be actually preprocessed, however, is not always fixed. Using a fixed number of solid-phase extraction columns (96 pieces), as in the conventional technique, therefore, has usually caused some of the wells (solid-phase extraction columns) to remain unused. A decrease in efficiency was thus inevitable, where relative cost of analysis increased, and waste disposal volume increased.

In addition to the above-mentioned problem of deterioration in cost performance, when specimens are needed to be analyzed chronologically sequentially and randomly, a problem such that preprocessing of the next specimen can not be started until the earlier started preprocessing is completed occurs. That is, specimens can not be continuously loaded into the preprocessing apparatus. This leads to an increase in turn-around-time (TAT), a waiting time taken until analytical results are obtained.

Further, whereas the well plate that forms the large number of wells (96 pieces) allows simultaneous movement of the specimens accommodated in the wells, the well plate itself is of a relatively large size. Due to this, spaces are required for storage/retraction of the well plates, for operations such as dispensing, mixing, pressurization, and filtering, for installing the devices required for movement and various processing operations, and the like. As a result, reduction in the size of apparatuses has been obstructed.

Patent Documents 2 and 3 relate to known examples of an automatic analyzer, which conducts optical measurement after executing preprocessing for separation/extraction of target constituents by causing reactions with a reaction reagent that contains magnetic beads, and separating/extracting analytic molecules. The Patent Documents 2, 3 also discloses a technique relating to a disposable dispensing pipette used for preprocessing, for reducing carry-over. These conventional techniques, unlike the technique in Patent Document 1, employ sequential preprocessing, not batch-based preprocessing. Therefore, the disadvantages of the technique in Patent Document 1, that is, disadvantages appearing when a specific number of specimens (96 pieces) is not reached, such as the analytical cost increase, waste parts increase, and TAT increase due to incapability of continuous loading can be avoided. In these known techniques, however, as described in Patent Document 3, if dispensing/mixing is conducted so as to achieve minimum carry-over for each of a plurality of reaction steps in preprocessing, related parts need to be replaced with new disposable parts for each step of reactions, during a first reagent step and a second reagent step. This replacement has led to increases in the number of disposable parts consumed and the number of disposable parts to be retained by devices.

RELATED ART LITERATURE

Patent Documents

Patent Document 1: JP-2006-007081-A
Patent Document 2: JP-2000-105248-A
Patent Document 3: JP-2000-235037-A Non-Patent Documents Non-Patent Document 1: Thomas M. Annesley, Larry Clayton: "Simple Extraction Protocol for Analysis of Immunosuppressant Drugs in Whole Blood", Clinical Chemistry, vol. 50, pp. 1845-1848 (2004)

SUMMARY OF THE INVENTION

Problems to be Solved by the Invention

In order to solve the foregoing problems, an object of the present invention is to provide a separating, extracting, and filtering method of a low carry-over ratio, this method being capable of sequential loading and preprocessing of a large number of specimens to be implemented with a minimal number of disposable parts. This allows, irrespective of the number of specimens, cost-efficient, short-TAT, and rapid separation and extraction at a low carry-over rate and without an unnecessary waste of parts such as found in batch processing.

Means for Solving the Problems

In order to attain the above object, a specimen processing system according to the present invention includes: means disposed circularly to transport a reaction vessel for separating and extracting target substances from a specimen to be processed; a plurality of processing steps, which are executed along a reaction vessel transport line of the transporting means, to conduct various processes upon the specimen to be processed that is accommodated in the reaction vessel; suctioning and discharging means that dispenses the specimen to be processed, from a specimen container supplied to the processing system, into the reaction vessel; and filtering means that uses the reaction vessel.

The suctioning and discharging means includes driving means that moves the suctioning and discharging means in a plurality of preprocessing steps so that in addition to the dispensing of the specimen, the suctioning and discharging means conducts mixing by being immersed in the specimen accommodated in the reaction vessel and suctioning and discharging a portion of the specimen.

Additionally, the reaction vessel is constructed to prevent carry-over and a loss of a preprocessing solution from occurring between steps, by integrating the filtering means and a collection vessel to collect the filtered solution. The reaction vessel further enables efficient supply of a filtrate to a solid-phase extraction section by taking a configuration in which the filtering means is connected to the solid-phase extraction section that is positioned at a downstream side of the filtering means.

Furthermore, the filtering vessel section and the solid-phase extraction section are connected removably to each other in the reaction vessel. After filtering, the filtering vessel section is separated from the solid-phase extraction section to remove rapidly and efficiently a precipitate and other substances left in the filtering vessel section. This easily prevents impurities from being redissolved and leaking from the filtered precipitate during washing and eluting phases of solid-phase extraction.

Hence, one disposable pipette/nozzle tip part for specimen suctioning and discharging can be shared during practically all phases of specimen dispensing and mixing in a plurality of reaction steps. Moreover, filtering and a solution collection step subsequent thereto can be executed with one disposable container/vessel, so that preprocessing can be achieved efficiently with short TAT and low carry-over.

Effects of the Invention

The present invention provides a rapid processing system that uses a minimum number of low-carryover disposable parts, suppresses a decrease in cost performance, and has high collection efficiency and a compact apparatus configuration.

BRIEF DESCRIPTION OF THE DRAWINGS

FIG. 10 is a table that lists processing steps relating to the specimen processing system according to the third embodiment of the present invention;

MODES FOR CARRYING OUT THE INVENTION

Embodiments of the present invention will be described below referring to the accompanying drawings.

In the following embodiments, a specimen processing system is described as an example, which is used to preprocess whole-blood specimens for measurement of a concentration of an immunosuppressant drug in whole blood by means of liquid chromatography-mass spectrometry. This processing system extracts desired constituents by removing blood cell constituents and protein constituents of whole blood through filtering separation after condensing and precipitating the constituents, which are likely to interfere with liquid chromatography-mass spectrometry at a following stage.

First Embodiment

A first embodiment is characterized in that a dispensing/mixing mechanism that dispenses specimens and mixes reaction solutions is present on the same axis as that of a turntable having reaction vessels arranged thereon, and also characterized in that each reaction vessel is configured by a filtering vessel section and a collection unit which are integrated and removable.

Figure 1:
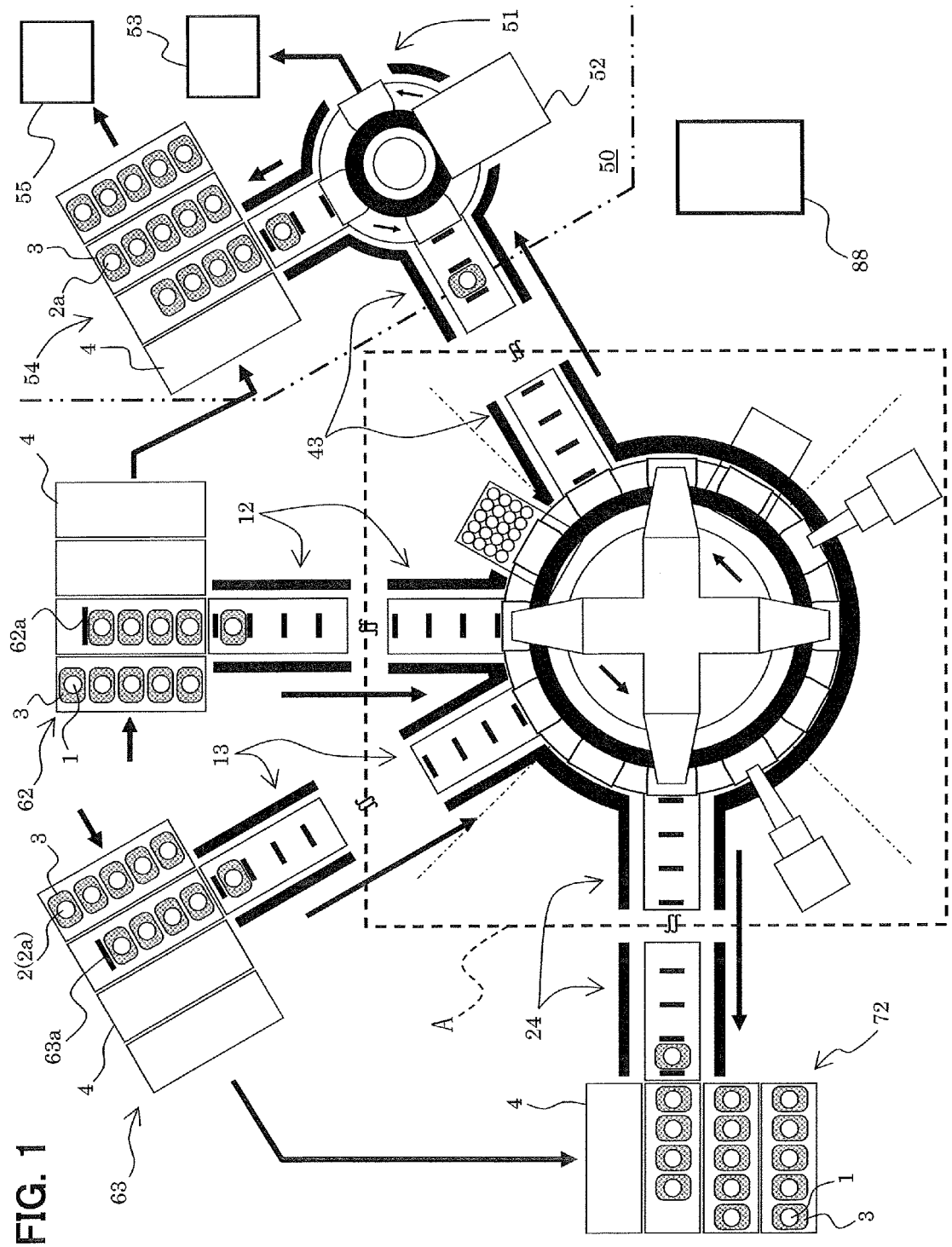
FIG. 1 is a plan view schematically showing a total specimen processing system configuration according to a first embodiment of the present invention.
Figure 2:
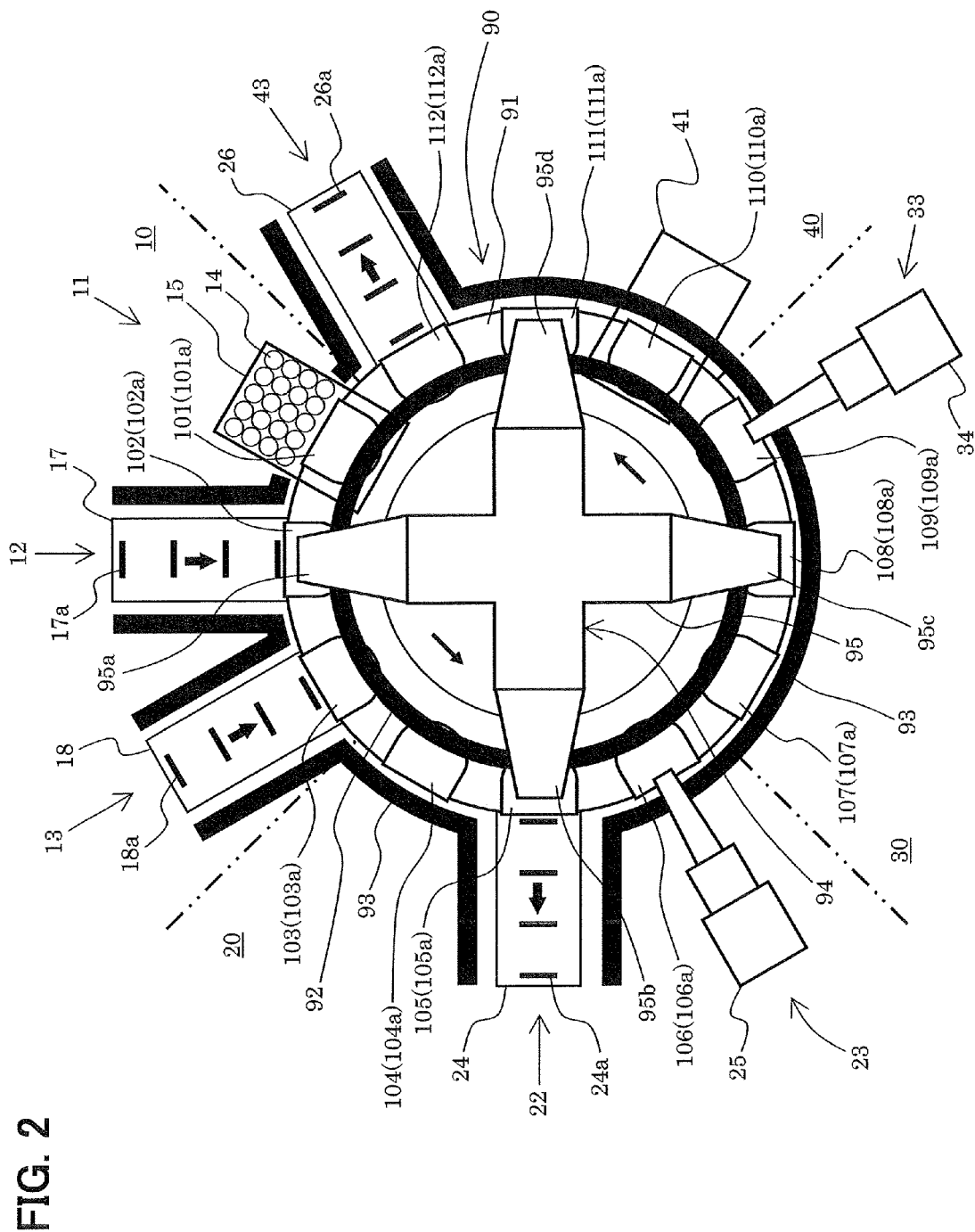
FIG. 2 is an enlarged view of section A shown in FIG. 1.
Figure 3:
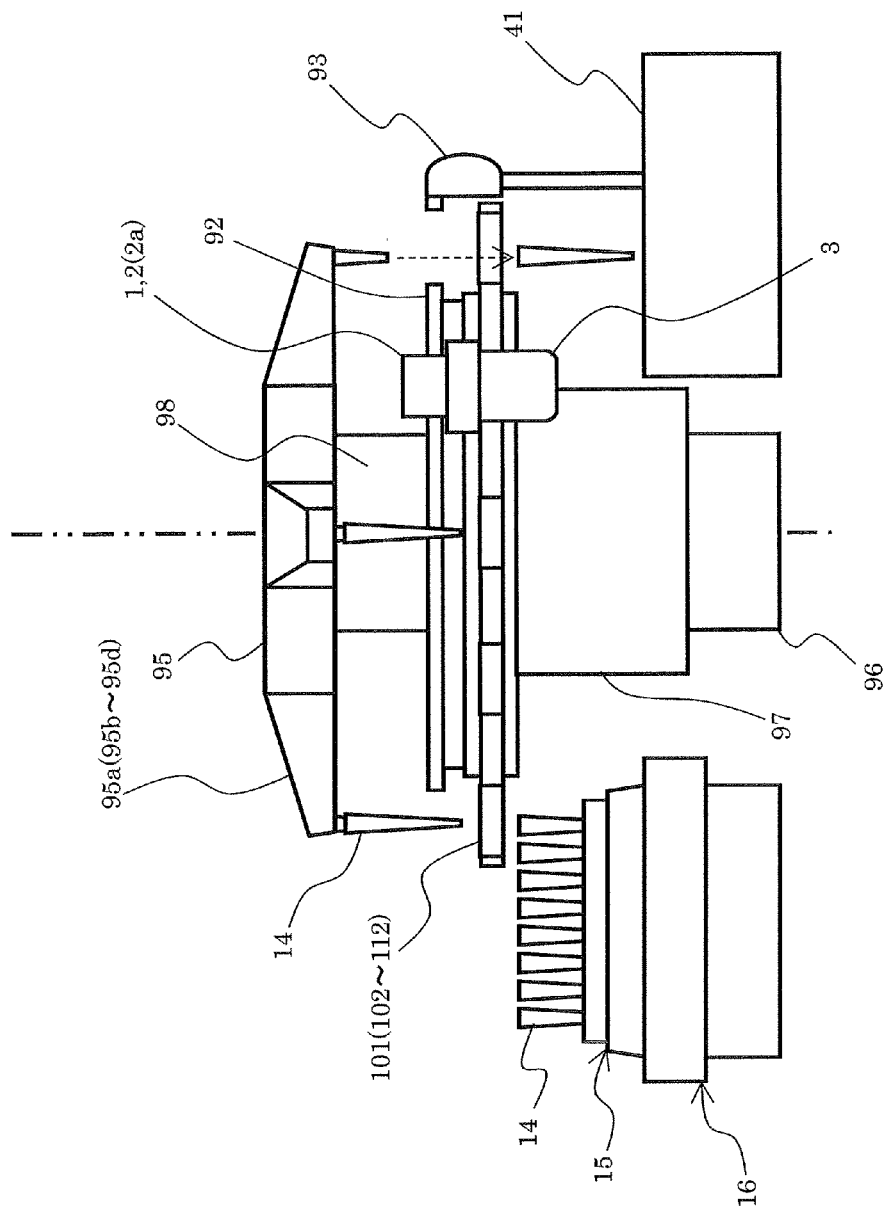
FIG. 3 is a first side view schematically representing a relationship in position between constituent elements of the system shown in FIG. 2.
Figure 4:
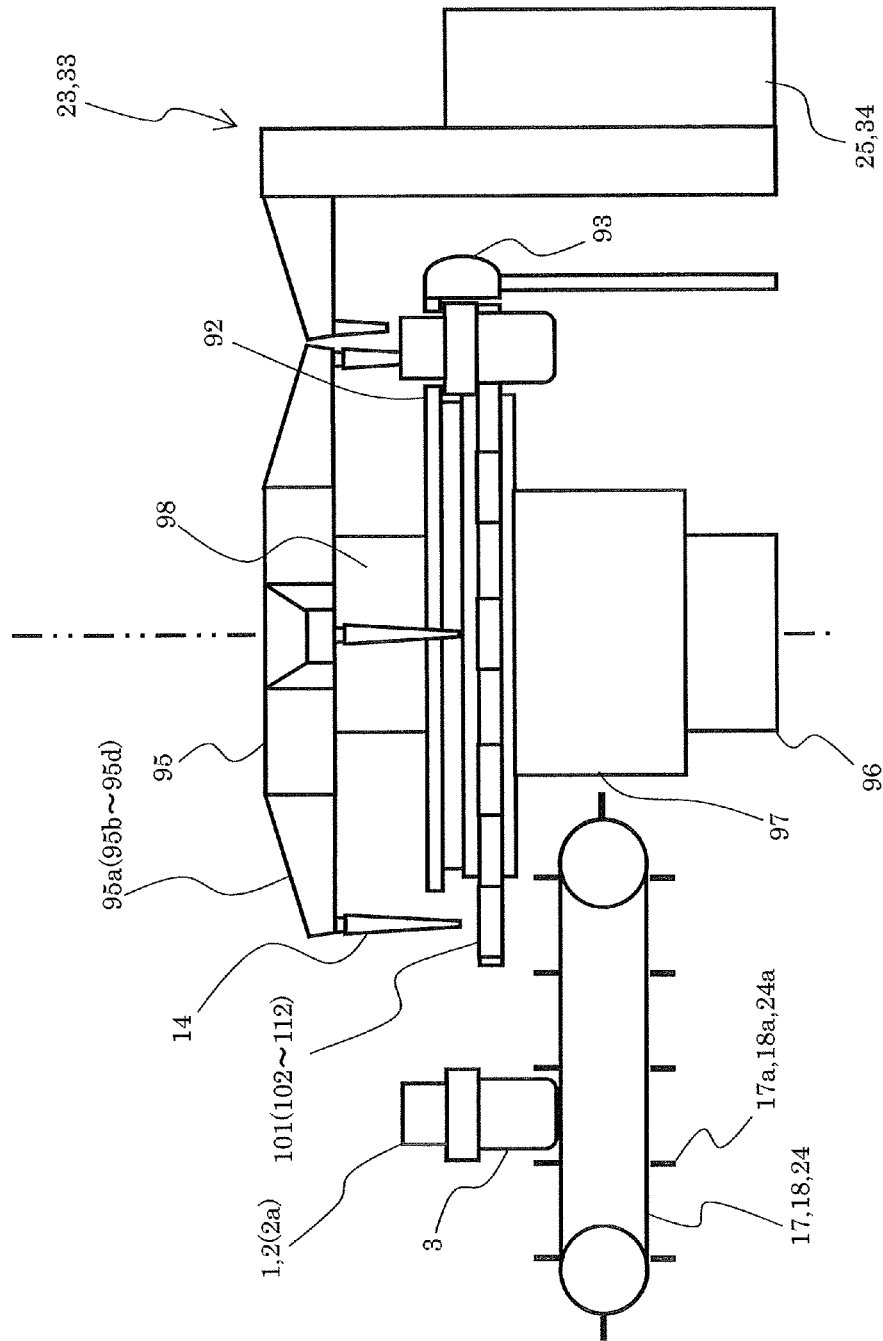
FIG. 4 is a second side view schematically representing a relationship in position between the system constituent elements shown in FIG. 2.
Figure 14:
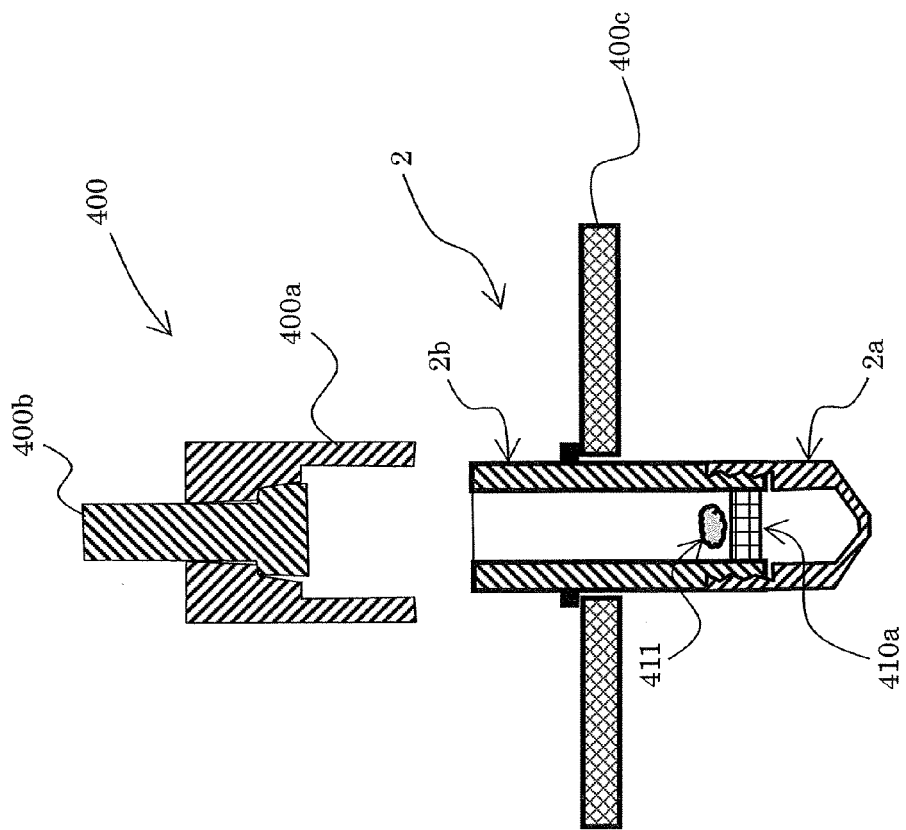
FIG. 14 is a cross-sectional view showing a pressurizer, reaction vessel, and collection vessel section of either the first or second embodiment of the present invention.

FIG. 1 is a plan view schematically showing a total specimen processing system configuration according to the present embodiment, and FIG. 2 is an enlarged view of section A in FIG. 1. FIGS. 3 and 4 are side views schematically representing a positional relationship of elements constituting the system shown in FIG. 2. FIG. 14 is a cross-sectional view showing a reaction vessel used in the present embodiment.

Referring to FIGS. 1 and 2, the specimen processing system according to the present embodiment includes: specimen containers 1 each containing a whole-blood specimen to be processed; reaction vessels 2 in which the target specimens (whole-blood specimens) are processed in various steps; a transport mechanism 90 that holds and transports each specimen container 1 and each reaction vessel 2; a dispensing unit 10 that dispenses the target specimen (whole-blood specimen) from the specimen container 1 to the reaction vessel 2; a hemolyzing unit 20 that hemolyzes the target specimen (whole-blood specimen) accommodated in the cartridge 2; a protein precipitating unit 30 that conducts a protein precipitation process upon the hemolyzed target specimen; a reaction vessel collection unit 40 that collects the reaction vessel 2 containing the target specimen which has been subjected to protein precipitation; a precipitate removing unit 50 that removes proteins from the target specimen accommodated in the collected reaction vessel 2; a dispensing/mixing mechanism 94 (suctioning/discharging means) that conducts dispensing and mixing by suctioning/discharging the target specimen accommodated in the specimen container 1 and the reaction vessel 2; a specimen container supply unit 62 that supplies the specimen container 1 to the dispensing unit 10; a reaction vessel supply unit 63 that supplies the reaction vessel 2 to the dispensing unit 10; a specimen container collection unit 72 that collects the specimen container 1 from the hemolyzing unit 20; and a total control unit 88 that controls operation of the entire specimen processing system.

Next, each constituent element of the specimen processing system according to the present embodiment is described in detail below referring to FIGS. 3 and 4 in addition to FIGS. 1 and 2.

The specimen containers 1 and reaction vessels 2 in the specimen processing system of the present embodiment are loaded within specimen container holders 3 whose forms have identical specifications. The specimen container holders 3 each have an opening (not shown) such that it can stably hold a specimen container 1 or a reaction vessel 2 whose shape may vary. Therefore, even if specimen containers or reaction vessels of different shapes are used, they can be handled in substantially the same way and stably transported by mounting them in the specimen container holders 3. Unless expressly noted in the following description, it is to be understood that the specimen containers 1 and the reaction vessels 2 (both are hereinafter referred to collectively as specimen containers) are loaded within the specimen container holders 3.

As shown in FIG. 14, each reaction vessel 2 includes a filtering vessel section 2b having a filter 410a at bottom, and a collection vessel section 2a for collecting and accommodating a filtrate that has been passed through the filter 410a, and the filtering vessel section 2b and the collection vessel section 2a are connected to each other (in FIGS. 1-4, the collection vessel section 2a has its reference number shown with parentheses).

Under a no-pressure state, various solutions and target specimen stay in effect within the filtering vessel section 2b, because they pass through the filter 410a very slowly. Under this state, the precipitate removing unit 50 uses a pressurizing mechanism 52 inside it to apply pressure to the inside of the filtering vessel section 2b. Predetermined constituents then pass through the filter 410a and are placed in the collection vessel section 2a. This process is hereinafter termed "filtering". Filtering is not limited to be conducted by using a method of pressurizing the inside of the filtering vessel section 2b, and may instead use, for example, a method of applying a negative pressure to the collection vessel section 2a, or a method of centrifuging the reaction vessel 2.

The reaction vessel 2 has construction that is capable of separating the filtering vessel section 2b from the collection vessel section 2a after filtering, and hence, efficient low-carryover collection of the filtrate can be achieved.

Each specimen container 1 and reaction vessel 2, that is, each specimen container is provided with an individual identification label (e.g., a bar code: not shown) for identifying each of the specimen containers used in the specimen processing system. Information on the target specimens accommodated in the specimen containers having the individual identification labels is prestored within a storage section (not shown) of the total control unit 88, in association with the particular individual identification label.

The transport mechanism 90 includes: a turntable 91 having a circular outer circumference with a vertically directed rotational axis as its center; a plurality of (e.g., 12) openings, 101 to 112 (retainers), provided at an equal spacing in a circumferential direction on the outer circumference of the turntable 91, for retaining specimen containers 1 and reaction vessels 2 (i.e., specimen containers) loaded within the specimen container holders 3; a specimen container holder-retaining member 92 that suppresses upward movement of each specimen container holder 3 accommodating the specimen container 1 or reaction vessel 2 retained by each opening 101-112; a specimen container holder anti-drop guard 93 that prevents the specimen container holder 3 accommodating the specimen container 1 or reaction vessel 2, from moving in a radially outward direction of the turntable 91 and dropping therefrom; and a rotation driving mechanism 97 that rotates the turntable 91 in a circumferential direction.

The openings 101-112 are provided in counterclockwise order of the serial reference number, that is, 101 to 112 in counterclockwise order, on the outer circumference of the turntable 91 in FIG. 2, so that the openings 101 and 112 are next to each other. Further, each opening 101-112, constructed to retain one specimen container holder 3, retains the specimen container 1 or the reaction vessel 2 by retaining the specimen container holder 3. Furthermore, each opening 101-112 has a sensor (not shown) that detects whether the opening retains the specimen container holder 3, that is, presence/absence of the specimen container holder 3. The sensor, after detecting the presence/absence of the specimen container holder 3 at the opening 101-112, transmits detection results to the total control unit 88.

In the transport mechanism 90, the rotation driving mechanism 97 drives the turntable 91 to rotate in the circumferential direction (counterclockwise in FIG. 2) with the opening 101-112 retaining the specimen container holder 3 which accommodates the specimen container 1 or the reaction vessel 2. The specimen container 1 or the reaction vessel 2 can thereby be transported to respective processing units. That is to say, the openings 101-112 on the outer circumference of the turntable 91 constitute the transport means for carrying the specimen containers (specimen containers 1, reaction vessels 2), which are each annularly arranged and each contain the specimen to be processed.

A plurality of (e.g., four) processing units detailed later herein, namely, a dispensing unit 10, a hemolyzing unit 20, a protein precipitating unit 30, and a reaction vessel collection unit 40, are arranged along a transport line provided by the above-mentioned transport means to carry the specimen containers. Three adjacent openings are used as a set for processing at each of the processing units 10 to 40. The openings 101-112 are sorted into three kinds according to their roles (functions). A first kind consists of the openings 101, 104, 107, and 110 related to processing of puppet/nozzle tips 14, a second kind consists of the openings 102, 105, 108, and 111 related to the processing of the specimen containers 1, and a third kind consists of the openings 103, 106, 109, and 112 related to the processing of the reaction vessels 2. In other words, three adjacent openings form one set, so that the openings contained in the set each perform a specific, different function.

When positions of the openings 101-112 shown in FIG. 2 are defined as the initial positions, stopping positions 101a to 112a are defined as the respective initial layout positions of the openings 101-112. The reference numbers of the stopping positions 101a-112a are shown with parentheses in FIG. 2. The stopping positions 101a-112a, as with the openings 101-112, are provided in counterclockwise order of the serial reference number, that is, 101a to 112a in counterclockwise order, at an equal spacing on the outer circumference of the turntable 91, so that the stopping positions 101a and 112a are next to each other. Rotation of the turntable 91 moves the openings 101-112 in the numerical order of the stopping positions 101a-112a. A distance between two adjacent stopping positions is defined as one pitch. For example, when the opening 101 at the stopping position 101a moves to the stopping position 102a, this means that the opening has moved through one pitch.

The same number of stopping positions are provided at the dispensing unit 10, the hemolyzing unit 20, the protein precipitating unit 30, and the reaction vessel collection unit 40 each. The stopping positions 101a-103a, 104a-106a, 107a-109a, and 110a-112a constitute part of the dispensing unit 10, the hemolyzing unit 20, the protein precipitating unit 30, and the reaction vessel collection unit 40, respectively.

The dispensing/mixing mechanism 94 (suctioning/discharging means) includes: a base 95 provided above the transport mechanism 90 and constructed to rotate about the same axis as that of the turntable 91; a plurality of (e.g., four) nozzles, 95a to 95d, arranged circularly around the rotational axis of the base 95, each nozzle having a distal end directed downward, over the line of movement of each opening 101-112; a suctioning/discharging mechanism 96 connected to the nozzles 95a-95d via a pipeline not shown, for activating the nozzles 95a-95d to suction/discharge the specimen to be processed; disposable nozzle tips 14 each removably provided at the distal end of one of the nozzles 95a-95d; and a driving mechanism 98 that drives the base 95 vertically and rotationally.

Upon the base 95 being rotationally driven by the driving mechanism 98, the nozzles 95a-95d move along the line of movement of the specimen containers (specimen containers 1, reaction vessels 2) retained by the transport mechanism 90. The nozzles 95a-95d, therefore, have a line of movement that is positioned over that of the specimen containers (specimen containers 1, reaction vessels 2).

The number of nozzles 95a-95d provided in the dispensing/mixing mechanism 94 is set to be the same as the number of processing units (in the present embodiment, four nozzles/units) that are provided along the transport line on the transport mechanism 90. The nozzles 95a-95d are arranged at an equal spacing in a rotational direction of the base 95. Therefore, for example, if as shown in FIG. 2, the nozzle 95a is positioned over the stopping position 102a, the nozzles 95b, 95c, 95d are positioned over the stopping positions 105a, 108a, 111a, respectively.

The thus-constructed dispensing/mixing mechanism 94 conducts dispensing and mixing as follows. First, the driving mechanism 98 drives the base 95 to rotate. The nozzles 95a-95d, each with a nozzle tip 14 mounted thereupon, are stopped over the specimen containers (specimen containers 1, reaction vessels 2) retained at the openings 101-112, so as to be arranged to face the openings in each specimen container. Next, the driving mechanism 98 moves the base 95 downward and immerses one nozzle tip 14 in the target specimen accommodated in one specimen container. Then, the suctioning/discharging mechanism 96 suctions the target specimen into the nozzle tip 14 (this operation is hereinafter termed "suction process"). At this time, if the target specimen is to be mixed, the nozzle tip 14 repeats discharging and suctioning operations (these operations are hereinafter termed "mixing process"). Further, if the target specimen is to be dispensed, the driving mechanism 98 raises the base 95 with the target specimen suctioned in the nozzle tip 14. The nozzle tip 14 is stopped over the specimen container retained at one of the openings 101-112, to face the opening in the specimen container, and the driving mechanism 98 then lowers the base 95. The target specimen suctioned in the nozzle tip 14 is discharged into a reaction vessel 2 by the suctioning/discharging mechanism 96 (this operation is hereinafter termed "discharge process").

The dispensing unit 10 includes: a nozzle tip supply unit 11, provided at the stopping position 101a, for mounting a disposable nozzle tip 14 on the nozzle 95a-95d that has stopped at the stopping position 101a (this operation is hereinafter termed "nozzle tip-mounting process"); a specimen container supply line 12, provided at the stopping position 102a, for supplying a specimen container 1 containing the target specimen (whole-blood specimen) to the opening (e.g. in FIG. 2, opening 102) that has stopped at the stopping position 102a (this operation is hereinafter termed "specimen container supply process"); and a reaction vessel supply line 13, provided at the stopping position 103a, for supplying a reaction vessel 2 used to accommodate and process the target specimen, to the opening (e.g. in FIG. 2, opening 103) that has stopped at the stopping position 103a (this operation is hereinafter termed "reaction vessel supply process").

As shown in FIGS. 2 and 3, the nozzle tip supply unit 11 includes a nozzle tip rack 15 having a plurality of disposable nozzle tips 14 stored therein, and a nozzle tip rack moving mechanism 16 that drives the nozzle tip rack 15 to move in horizontal and vertical directions. The nozzle tip rack moving mechanism 16 moves the nozzle tip rack 15 so that one of the nozzle tips 14 accommodated therein is disposed under the opening (e.g. in FIG. 2, opening 101) that has stopped at the stopping position 101a. On the other hand, one of the nozzles 95a-95d not having a nozzle tip 14 is disposed over the stopping position 101a. Then, the driving mechanism 98 lowers the base 95 to a predetermined height to equip the above-mentioned nozzle 95a-95d above-mentioned with the nozzle tip 14 in the nozzle tip rack 15.

The specimen container supply line 12 includes a belt conveyor 17 that carries the specimen container 1 within one specimen container holder 3, from a specimen container supply unit 62 (described later herein) to the transport mechanism 90, and a specimen container holder positioning partition 17a that appropriately positions the specimen container holder 3 with respect to the belt conveyor 17 and suppresses slipping of the holder on the conveyor. After stopping a desired opening (e.g. in FIG. 2, the opening 102) at the stopping position 102a by rotating the turntable 91 of the transport mechanism 90, the processing system actuates the belt conveyor 17 to supply the specimen container holder 3 containing the specimen container 1 to that opening and retain the holder 3 at the opening.

The reaction vessel supply line 13 includes a belt conveyor 18 that carries the reaction vessel container 2 within one specimen container holder 3, from a reaction vessel supply unit 63 (described later herein), and a specimen container holder positioning partition 18a that appropriately positions the holder 3 with respect to the belt conveyor 18 and suppresses slipping of the holder on the conveyor 18. After stopping a desired opening (e.g. in FIG. 2, the opening 103) at the stopping position 103a by rotating the turntable 91 of the transport mechanism 90, the processing system actuates the belt conveyor 18 to supply the specimen container holder 3 containing the reaction vessel 2 to that opening and retain the holder 3 at the opening.

The specimen container supply unit 62 includes at least one specimen container rack 4 in which the specimen containers 1 containing the target specimen (whole-blood specimen) are accommodated in individual specimen container holders 3, and a delivering mechanism 62a that delivers the specimen containers 1 and the specimen container holders 3 within each specimen container rack 4 to the belt conveyor 12 integrally.

A plurality of (e.g., five) specimen containers 1 in the specimen container holders 3 are accommodated in line in the specimen container rack 4. After disposing this rack at one end of the belt conveyor 12 that is closer to the specimen container supply unit, the specimen containers are unloaded (delivered), one at a time, to the belt conveyor 12 by the delivering mechanism 62a. When the specimen container rack 4 is emptied by unloading all of the accommodated specimen containers 1, the specimen container rack 4 is carried to the precipitate removing unit 50 via a transport line not shown. New specimen container racks 4 having specimen container holders 3 loaded with the specimen containers 1, containing the target specimens, would be sequentially sent to the specimen container supply unit 62. The transport destination of the empty specimen container rack 4 does not need to be the precipitate removing unit 50, and may instead be, for example, a specimen container collection unit 72 (described later herein) that uses empty specimen container racks 4.

The reaction vessel supply unit 63 includes at least one specimen container rack 4 in which the reaction vessels 2 containing the target specimen (whole-blood specimen) and used to conduct various processes are accommodated in individual specimen container holders 3, and a delivering mechanism 63a that delivers the reaction vessels 2 and the specimen container holders 3 within each specimen container rack 4 to the belt conveyor 13 integrally.

A plurality of (e.g., five) reaction vessel 2 in the specimen container holders 3 are accommodated in line in the specimen container rack 4. After disposing this rack at one end of the belt conveyor 13 that is closer to the reaction vessel supply unit, the reaction vessels are unloaded (delivered), one at a time, to the belt conveyor 13 by the delivering mechanism 63a. The specimen container rack 4, after being emptied by the unloading of all accommodated reaction vessels 2, is carried to the specimen container collection unit 72 via a transport line not shown. Then, the reaction vessel supply unit 63 is sequentially refilled with new specimen container racks 4 each having specimen container holders 3 loaded with reaction vessels 2. The transport destination of the empty specimen container rack 4 does not need to be the specimen container collection unit 72 and may instead be, for example, the precipitate removing unit 50 (described later herein) that uses empty racks 4. In addition, if the kind of reaction vessel 2 differs according to the sort of specimen or measurement item, a reaction vessel 2 appropriate for the particular specimen or measurement item may be supplied based on an instruction given from the total control unit 88.

The hemolyzing unit 20 includes a specimen container collection line 22 provided at the stopping position 105a and used to collect a specimen container 1 retained at the opening (e.g. in FIG. 2, opening 105) that has stopped at the stopping position 105a (the collection is hereinafter termed "specimen container collection process"). The hemolyzing unit 20 also includes a hemolyzing solution injector 23 provided at the stopping position 106a and used to inject a hemolyzing solution as a first reagent into a reaction vessel 2 retained at the opening (e.g. in FIG. opening 106) that has stopped at the stopping position 106a (the injection is hereinafter termed "hemolyzing solution injection process"). The stopping position 104a is a standby position for an opening not retaining a specimen container holder 3.

The specimen container collection line 22 includes a belt conveyor 24 that carries the specimen container 1 within a specimen container holder 3, from the transport mechanism 90 to the specimen container collection unit 72, and a specimen container holder positioning partition 24a that appropriately positions the specimen container holder 3 with respect to the belt conveyor 24 and suppresses slipping of the holder on the conveyor 24. After stopping a desired opening (e.g. in FIG. 2, the opening 105) at the stopping position 105a by rotating the turntable 91 of the transport mechanism 90, the processing system actuates the belt conveyor 24 to collect from that opening the specimen container holder 3 containing the specimen container 1.

The hemolyzing solution injector 23 includes a solution tank 25 holding the hemolyzing solution for hemolyzing the target specimen (whole-blood specimen) accommodated in the reaction vessel 2.

The hemolyzing solution injected into the target specimen (whole-blood specimen) is, for example, water or a zinc sulfate solution also used for ZTT (Zinc sulfate Turbidity Testing). When water is used for hemolysis, the hemolysis is caused by diluting the concentration of the target specimen (whole-blood specimen) to a 0.35%-0.50% NaCl equivalent (normal saline solutions generally have a concentration equivalent to 0.90% NaCl). This is a method based on the principle of blood cell bursting caused by hypotonization. The salt concentrations of blood are diluted to reduce an osmotic pressure around the blood cells, to thereby cause excessive uptake of water into the blood cells. This in turn ruptures the cell membranes and causes hemolysis. This method also provides a viscosity reduction effect, as well as a hemolyzing effect, against a significantly viscous specimen such as a blood specimen sampled from a patient with hyperlipidemia, and is therefore expected to facilitate constituent extraction from hemolyzed blood. As mentioned, the hemolyzing solution may be a zinc-sulfate-containing solution that is a water-soluble deproteinizing agent. The hemolyzing effect obtained in this case is based on the same principle as the hemolyzation using water, bursting blood cells by osmotic pressure. In addition, since zinc sulfate provides the chelating effect of the zinc to condense and precipitate γ-globulin and other key proteins present in large quantities in blood, deproteinization can be simultaneously conducted with hemolyzation.

The protein precipitating unit 30 includes a protein-precipitating solution injector 33 provided at the stopping position 109a, used to inject a protein-precipitating solution as a second reagent into the reaction vessel 2 retained at the opening (e.g. in FIG. 2, opening 109) that has stopped at the stopping position 109a (the injection is hereinafter termed "protein-precipitating solution injection process"). The stopping positions 107a and 108a are standby positions for openings not retaining a specimen container holder 3.

The protein-precipitating solution injector 33 includes a solvent tank 34 holding the protein-precipitating solution for conducting a protein-precipitating process upon the target specimen (whole-blood specimen) accommodated in the reaction vessel 2.

The protein-precipitating solution injected into the target specimen (whole-blood specimen) is an organic solvent, such as methanol. Upon an organic solvent being added to a hemolyzed target specimen, the target constituents adsorbed onto the proteins in the target specimen (blood) are extracted into the organic solvent, and simultaneously, the proteins are denatured (condensed) and precipitated. The condensed protein precipitate 411 is removed during deproteinization by the precipitate removing unit 50 described later herein.

Figure 5:
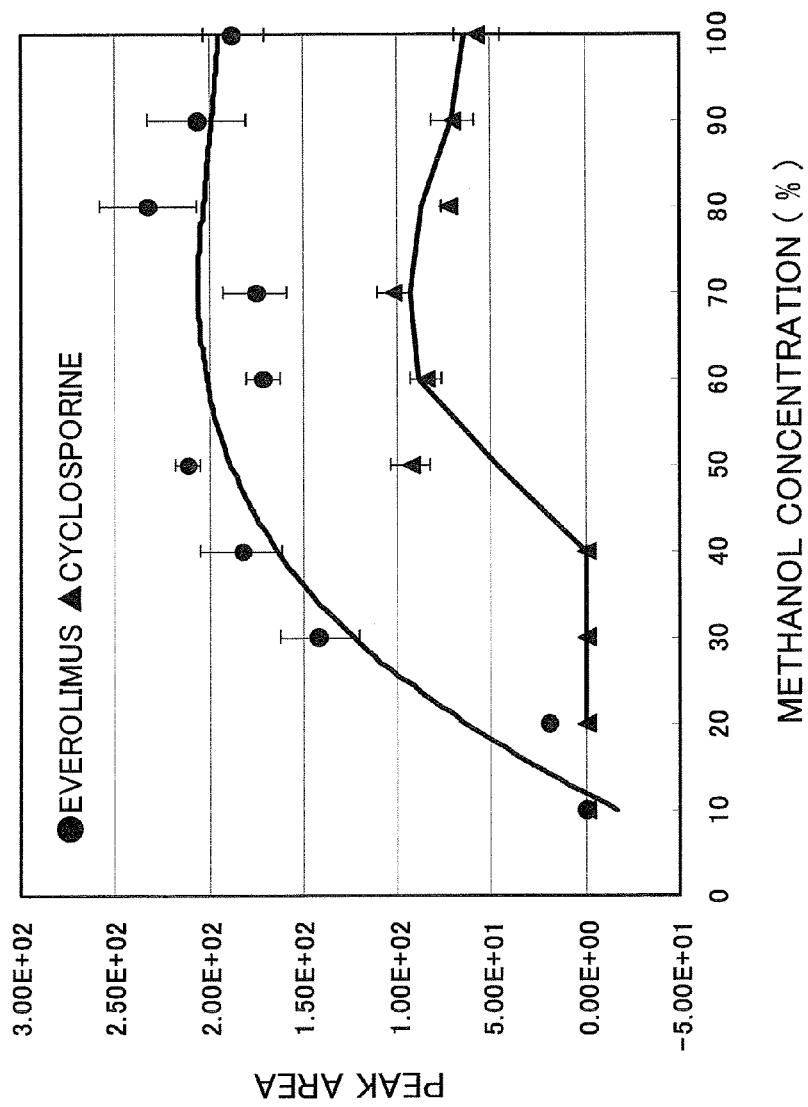
FIG. 5 is a diagram representing an example of a relationship between a concentration of an organic solvent and peak areas of desired constituents.

Solubility of the target constituents in an organic solvent depends on a concentration of the organic solvent. For example, such immunosuppressants as tacrolimus, sirolimus (rapamycin), everolimus, cyclosporine are highly hydrophobic and poorly soluble in aqueous solutions. Studies by the present inventors on solubility of some of these immunosuppressants in methanol, an organic solvent, indicate that the immunosuppressants tend to stably dissolve only when the concentration of methanol is 50% or more. FIG. 5 is a diagram representing an example of a relationship between a concentration of an organic solvent and peak areas of the desired constituents. In this case, everolimus and cyclosporine is taken as examples of the target constituents, and methanol as the organic solvent. As shown in FIG. 5, everolimus and cyclosporine tend to stably dissolve only when the concentration of methanol is 50% or more. Therefore, if these drugs are to be extracted as the target constituents, it is desirable that the concentration of methanol is at least 50%.

The reaction vessel collection unit 40 includes a nozzle tip discarder 41 provided at the stopping position 110a, used to remove and discard the disposable nozzle tip 14 mounted on the nozzle 95a-95d that has stopped at the stopping position 110a (the removal and discard of the nozzle tip is hereinafter termed "nozzle tip discarding process"). The reaction vessel collection unit 40 also includes a reaction vessel collection line 43 provided at the stopping position 112a, used to collect the reaction vessel 2 retained by the opening (e.g. in FIG. 2, opening 112) that has stopped at the stopping position 112a (the collection is hereinafter termed "reaction vessel collection process"). The stopping position 111a is a standby position for an opening not retaining a specimen container holder 3.

In the nozzle tip discarder 41, after the nozzle 95a-95d with the nozzle tip 14 has been disposed at the stopping position 110a, the nozzle tip 14 is dismounted from the nozzle 95a-95d by means of a predetermined mechanism, and the dismounted nozzle tip is discarded through the opening (e.g. in FIG. 2, opening 110) that has stopped at the stopping position 110a.

The reaction vessel collection line 43 includes a belt conveyor 26 that carries the reaction vessel 2 within a specimen container holder 3, from the transport mechanism 90 to the precipitate removing unit 50, and a specimen container holder positioning partition 26a that appropriately positions the specimen container holder 3 with respect to the belt conveyor 26 and suppresses slipping of the holder on the conveyor 26. After stopping a desired opening (e.g. in FIG. 2, the opening 112) at the stopping position 112a by rotating the turntable 91 of the transport mechanism 90, the processing system actuates the belt conveyor 26 to collect from that opening the specimen container holder 3 containing the reaction vessel 2, and carry the vessel 2 to the precipitate removing unit 50.

The precipitate removing unit 50 includes a transport mechanism 51 that receives the reaction vessel 2 carried in from the reaction vessel collection unit 40 by the belt conveyor 26 and transfers the reaction vessel 2, a pressurizing mechanism 52 that pressurizes the reaction vessel 2 transferred by the transport mechanism 51, a filter discarder 53 that collects and discards the filtering vessel section 2b of the pressurized reaction vessel 2, and an extract collection unit 54 that collects the collection vessel section 2a of the reaction vessel 2 and hence collects the filtrate accommodated in the vessel section 2a.

The pressurizing mechanism 52 pressurizes the inside of the filtering vessel section 2b of the reaction vessel 2 containing the target specimen to conduct filtering. The desired constituents are thereby passed through the filter and accommodated in the collection vessel section 2a. The protein precipitate 411 that has been condensed in the target specimen, in the protein precipitating unit 30, is removed by the filter within the reaction vessel 2 (deproteinized), and is collected along with the filtering vessel section into the filter discarder 53.

As shown in FIG. 14, the pressurizing mechanism 52 is equipped with a pressurizer 400 that includes a pressurizer holder 400a, a pressurizing syringe 400b, and a pressurizing base. The pressurizer holder 400a is mounted without a clearance on the filtering vessel section 2b.

The extract (target constituents) inside the collection vessel section 2a which has been collected into the extract collection unit 54, that is, the supernatant that has been collected after protein precipitation, is sent to a process site 55 for purification and measurement. The supernatant is, if needed, optionally dried up and redissolved using a dissolving solution for reduction in the amount of liquid and for concentration of the target constituents, and analyzed with a liquid chromatograph-mass spectrometer (LCMS) or the like. Thus, target constituents are separated/purified and detected, and identification and quantitative analysis of the constituents are conducted.

The total control unit 88, intended to control the operation of the entire specimen processing system, includes input means, storage means, display means, and more (none of them shown). Upon setup parameters for each constituent element of the system being entered by the input means, the total control unit 88 controls operation of each system element in accordance with software stored within the storage means, and executes preprocesses for the target specimen. In addition, if an unusual situation occurs in either of the processing units 10, 20, 30, 40, 50, 62, 63, 72, the total control unit 88 immediately suspends the operation of the entire specimen processing system and presents an alarm to a display device not shown.

Processing sequences in the specimen processing system of the present embodiment are next described below. The description assumes that during a start of preprocessing, the openings 101-112 are present at the respective initial positions shown in FIG. 2.

First, an operator loads a specimen container 1 containing the target specimen into a specimen container holder 3, stores this specimen container holder into a specimen container rack 4, and sets this rack on the specimen container supply unit 62. Additionally, the operator loads a reaction vessel 2 into another specimen container holder 3, stores this specimen container holder into another specimen container rack 4, and sets this rack on the reaction vessel supply unit 63. Under this state, the operator assigns a preprocessing start-up instruction using the input means (not shown) of the total control unit 88.

(Sequence 1)

The nozzle 95a moves to the stopping position 101a. At this time, the nozzles 95b, 95c, 95d move to the stopping positions 104a, 107a, 110a, respectively. Under this state, the processes described below are simultaneously conducted at the processing units 10, 20, 30, 40.

At the dispensing unit 10, a nozzle tip is mounted at the stopping position 101a, a specimen container is supplied to the opening 103 at the stopping position 103a, and a reaction vessel is supplied to the opening 103 at the stopping position 103a. The three processes are conducted at the same time.

At the hemolyzing unit 20, the specimen container is collected from the opening 105 at the stopping position 105a, and a hemolyzing solution is injected into the reaction vessel 2 retained by the opening 106 at the stopping position 106a. The nozzle 95b at the stopping position 104a merely moves in accordance with the nozzle 95a.

At the protein precipitating unit 30, a protein-precipitating solution is injected into the reaction vessel 2 retained by the opening 109 at the stopping position 109a. The nozzle 95c at the stopping position 107a merely moves in accordance with the nozzle 95a.

At the reaction vessel collection unit 40, the nozzle tip 14 is removed from the nozzle 95d at the stopping position 110a and discarded, and the reaction vessel is collected from the opening 112 at the stopping position 112a. Reaction vessels 2 that have been collected and then carried to the precipitate removing unit 50 are sequentially pressurized and collected into the extract collection unit 54.

(Sequence 2)

The nozzle 95a moves to the stopping position 102a. At this time, the nozzles 95b, 95c, 95d move to the stopping positions 105a, 108a, 111a, respectively. Under this state, the processes described below are simultaneously conducted at the processing units 10, 20, 30, 40.

At the dispensing unit 10, the contents of the specimen container 1 retained by the opening 102 at the stopping position 102a are mixed and suctioned. At the hemolyzing unit 20, the nozzle 95b at the stopping position 105a merely moves in accordance with the nozzle 95a.

At the protein precipitating unit 30, the nozzle 95c at the stopping position 108a merely moves in accordance with the nozzle 95a.

At the reaction vessel collection unit 40, the nozzle 95d at the stopping position 111a merely moves in accordance with the nozzle 95a.

(Sequence 3)

The nozzle 95a moves to the stopping position 103a. At this time, the nozzles 95b, 95c, 95d move to the stopping positions 106a, 109a, 112a, respectively. Under this state, the processes described below are simultaneously conducted at the processing units 10, 20, 30, 40.

At the dispensing unit 10, the target specimen is discharged into and then mixed in the reaction vessel 2 retained by the opening 103 at the stopping position 103a. At the hemolyzing unit 20, the contents of the reaction vessel 2 retained by the opening 106 at the stopping position 106a are mixed.

At the protein precipitating unit 30, the contents of the reaction vessel 2 retained by the opening 109 at the stopping position 109a are mixed.

At the reaction vessel collection unit 40, the nozzle 95d at the stopping position 112a merely moves in accordance with the nozzle 95a.

(Sequence 4)

The nozzle 95a moves to the stopping position 104a. At this time, the nozzles 95b, 95c, 95d move to the stopping positions 107a, 110a, 101a, respectively. In addition, at the same time that the nozzles 95a-95d move, the openings 101-112 move through three pitches counterclockwise. That is, the openings 110-112 move to the stopping positions 101a-103a, respectively, and the openings 101-109 move to the stopping positions 104a-112a, respectively.

At the state of layout after sequence 4, processes equivalent to the sequences 1 to 4 are repeated by regarding "nozzle 95d" as "nozzle 95a" and "openings 110-112" as "openings 101-103", and also by regarding the other parts "nozzles 95a-95c" and the "openings 101-109" correspondingly. Repeating the processes equivqlent to the sequences 1 to 4 in such a manner allows each process to be continuously conducted upon target specimens.

In conventional technology, since it is always necessary to use a fixed number of solid-phase extraction columns (96 pieces), some of the solid-phase extraction columns occasionally remain unused. Meanwhile, in the present embodiment of the above configuration, since one reaction vessel 2 is used for one target specimen, there is no need to always use a fixed number of solid-phase extraction columns, so an unused solid-phase extraction column does not occur. In addition, the conventional technology requires spaces for storage/retraction of the well plate, spaces for operation such as dispensing, mixing, pressurization, and filtering, and spaces for installation of devices used for various processing operations and movement. The present embodiment, however, reduces the space requirements. This is because the means that transports the specimen containers (specimen container 1, reaction vessel 2) accommodating the target specimen is annularly disposed, because a plurality of processing units, 10, 20, 30, 40, that conduct various processes on the target specimen accommodated in the specimen containers are arranged along the transport line provided by the transport means to carry the specimen containers, because the system includes the dispensing/mixing mechanism 94 having a plurality of nozzles 95a-95d arranged along the specimen container transport line of the transport means in order to suction and discharge the target specimen, and because the driving mechanism 98 moves the nozzles 95a-95d by rotationally driving the dispensing/mixing mechanism 94 in the circumferential direction.

Further, the system has substantially no loss of the target constituents, because separation/purification and measurement can be executed after filtering is conducted in a reaction vessel 2 whose constituent parts, the filtering vessel section 2b and collection vessel section 2a, are integrated. Thereby, the system can repeat efficient, random, continuous filtering with substantially no loss of the target constituents.

Furthermore, since one nozzle is used throughout processing in the processing units 10, 20, 30, 40, the nozzle tip 14 mounted on either of the nozzles 95a-95d does not need to be replaced per processing unit 10, 20, 30, 40, and the number of nozzle tips 14 to be used for processing can therefore be reduced.

Briefly, the present embodiment minimizes unnecessary disposable parts, suppresses a decrease in cost performance, and thus implements the miniaturization of the devices.

Second Embodiment

Figure 6:
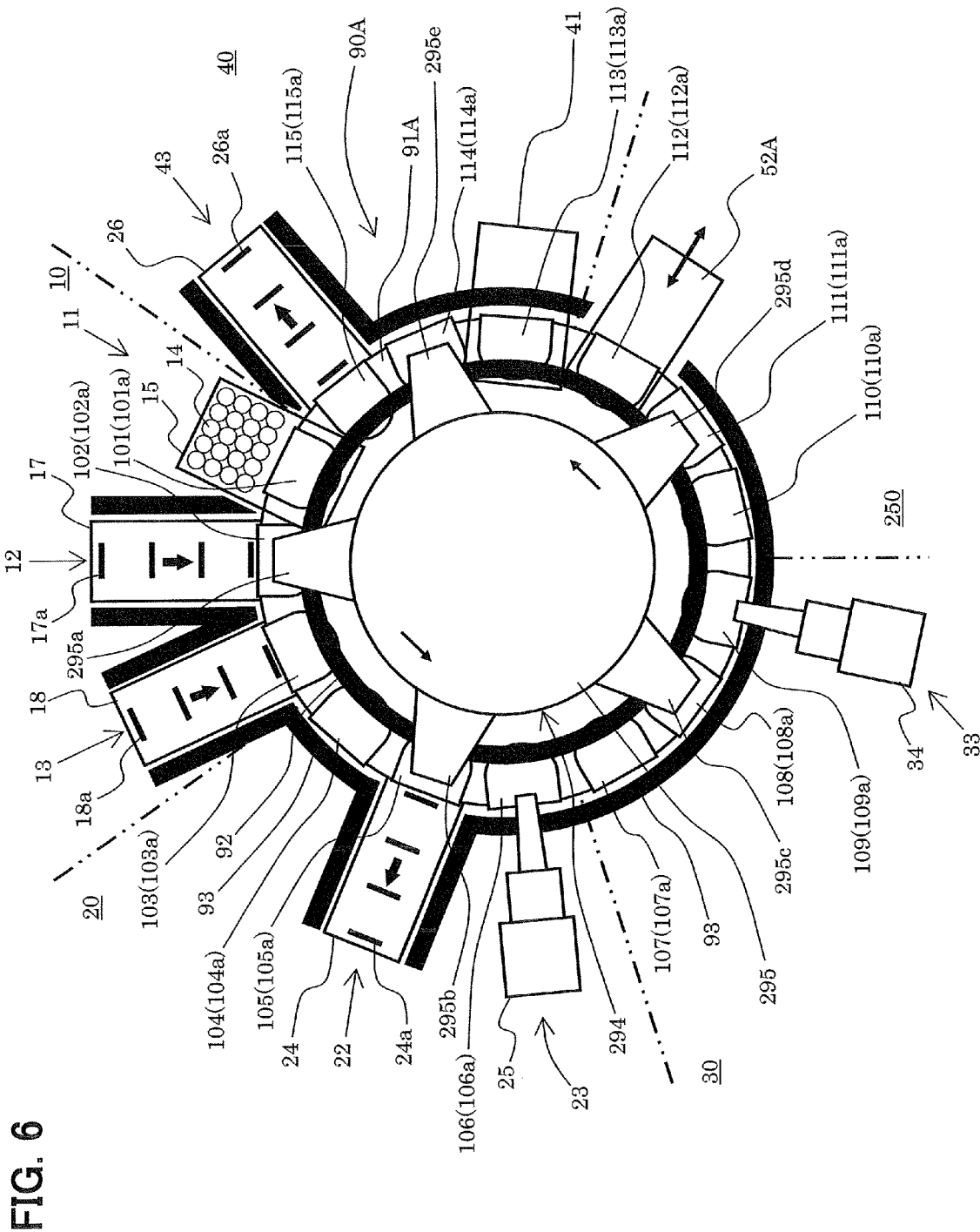
FIG. 6 is a detailed view of a section of a specimen processing system according to a second embodiment of the present invention, where only a configuration equivalent to section A of FIG. 1 is shown.

In a second embodiment of the present invention, a pressurizing unit 250 is added to the dispensing unit 10, hemolyzing unit 20, protein precipitating unit 30, and reaction vessel collection unit 40 arranged along the transport line of the transport mechanism 90 in the first embodiment. FIG. 6 is an enlarged view showing, of a specimen processing system according to the second embodiment of the present invention, only a transport mechanism 90A and its peripheral configuration. In FIG. 6, members equivalent to those shown in FIGS. 1 to 4 are each assigned the same reference number, and description of these elements is omitted.

Referring to FIG. 6, the transport mechanism 90A includes: a turntable 91A having a circular outer circumference with a vertically directed rotational axis as its center; a plurality of (e.g., 15) openings, 101 to 115 (retainers), provided at an equal spacing in a circumferential direction on the outer circumference of the turntable 91A, for retaining specimen containers 1 and reaction vessels 2 (i.e., specimen containers) loaded within specimen container holders 3; a specimen container holder-retaining member 92 that suppresses upward movement of each specimen container holder 3 accommodating the specimen container 1 or reaction vessel 2 retained by each opening 101-115; a specimen container holder anti-drop guard 93 that prevents the specimen container holder 3 accommodating the specimen container 1 or reaction vessel 2, from moving in a radially outward direction of the turntable 91A and dropping therefrom; and a rotation driving mechanism 97 (see FIG. 3, for example) that rotates the turntable 91A in a circumferential direction.

The openings 101-115 are provided in counterclockwise order of the serial reference number, that is, 101 to 115 in counterclockwise order, on the outer circumference of the turntable 91A in FIG. 6, so that the openings 101 and 115 are next to each other. In addition, each opening 101-115, constructed to retain one specimen container holder 3, retains the specimen container 1 or the reaction vessel 2 by retaining the specimen container holder 3. Furthermore, each opening 101-115 has a sensor (not shown) that detects whether the opening retains the specimen container holder 3, that is, presence/absence of the specimen container holder 3. The sensor, upon detecting the presence/absence of the specimen container holder 3 at the opening 101-115, transmits detection results to the total control unit 88.

The rotation driving mechanism 97 (see FIG. 3, for example) drives the turntable 91A to rotate in the circumferential direction (counterclockwise in FIG. 6) with the opening 101-115 retaining the specimen container holder 3, which accommodates the specimen container 1 or the reaction vessel 2. The transport mechanism 90A thereby carries the specimen container 1 or the reaction vessel 2 to respective processing units. That is to say, the openings 101-115 on the outer circumference of the turntable 91A constitute the transport means for carrying the specimen containers (specimen containers 1, reaction vessels 2), that are each annularly arranged and each contain the specimen to be processed.

A plurality of (e.g., five) processing units, namely, the dispensing unit 10, the hemolyzing unit 20, the protein precipitating unit 30, the pressurizing unit 250, and the reaction vessel collection unit 40, are arranged along a transport line provided by the transport means to carry the specimen containers. Three adjacent openings are used as a set for processing at each of the processing units 10, 20, 30, 250, 40. The openings 101-115 are sorted into three kinds according to role (function). A first kind consists of the openings 101, 104, 107, 110, and 113 related to processing of nozzle tips 14, a second kind consists of the openings 102, 105, 108, 111, and 114 related to the processing of the specimen containers 1, and a third kind consists of the openings 103, 106, 109, 112, and 115 related to the processing of the reaction vessels 2. In other words, three adjacent openings form one set, so that the openings contained in the set each perform a specific, different function.

When positions of the openings 101-115 shown in FIG. 6 are defined as initial positions, stopping positions 101a to 115a are defined at the respective layout positions of the openings 101-115 (the stopping positions 101a-115a are shown with parentheses in FIG. 6). The stopping positions 101a-115a, as with the openings 101-115, are provided in counterclockwise order of the serial reference number, that is, 101a to 115a in counterclockwise order, at an equal spacing on the outer circumference of the turntable 91A, so that the stopping positions 101a and 115a are next to each other. As the turntable 91A rotates, the openings 101-115 move in the numerical order of the stopping positions 101a-115a.

Same number of stopping positions are provided at the dispensing unit 10, the hemolyzing unit 20, the protein precipitating unit 30, the pressurizing unit 250, and the reaction vessel collection unit 40 each. The stopping positions 101a-103a, 104a-106a, 107a-109a, 110a-112a, and 113a-115a constitute part of the dispensing unit 10, the hemolyzing unit 20, the protein precipitating unit 30, the pressurizing unit 250, and the reaction vessel collection unit 40, respectively.

A dispensing/mixing mechanism 294 (suctioning/discharging means) includes: a base 295 provided above the transport mechanism 90A and constructed to rotate about the same axis as that of the turntable 91A; a plurality of (e.g., five) nozzles, 295a to 295e, arranged circularly around the rotational axis of the base 295, with each nozzle having a distal end directed downward, over a line of movement of each opening 101-115; a suctioning/discharging mechanism 96 (see FIG. 3, for example) connected to the nozzles 295a-295e via a pipeline not shown, for activating the nozzles 295a-295e to suction/discharge the specimen to be processed; disposable nozzle tips 14 each removably provided at the distal end of one of the nozzles 295a-295e; and a driving mechanism 98 (see FIG. 3, for example) that drives the base 295 vertically and rotationally.

Upon the base 295 being rotationally driven by the driving mechanism 98, the nozzles 295a-295e move along a line of movement of the specimen containers (specimen containers 1, reaction vessels 2) retained by the transport mechanism 90A. The nozzles 295a-295e, therefore, have a line of movement that is positioned over that of the specimen containers (specimen containers 1, reaction vessels 2).

The number of nozzles 295a-295e provided in the dispensing/mixing mechanism 294 is set to be the same as the number of processing units (in the present embodiment, five nozzles/units) that are provided along the transport line on the transport mechanism 90A. The nozzles 295a-295e are arranged at the equal spacing in a rotational direction of the base 295. Therefore, for example, if as shown in FIG. 6, the nozzle 295a is positioned over the stopping position 102a, the nozzles 295b, 295c, 295d, 295e are positioned over the stopping positions 105a, 108a, 111a, 114a, respectively.

The pressurizing unit 250 includes a pressurizing mechanism 52A provided at the stopping position 112a, for applying pressure to the reaction vessel 2 retained by the opening (e.g. in FIG. 6, opening 112) that has stopped at the stopping position 112a.

The stopping positions 110a and 111a are standby positions for openings not retaining a specimen container holder 3.

The pressurizing mechanism 52A, which conducts substantially the same process as that of the pressurizing mechanism 52 in the first embodiment, pressurizes the inside of the filtering vessel section 2b of the reaction vessel 2 containing the target specimen, and thus conducts filtering. The target constituents are then passed through the filter and accommodated in the collection vessel section 2a. The pressurizing mechanism 52A is also constructed to be capable of being retreated from the transport line of the transport mechanism 90A by a moving mechanism not shown.

The reaction vessel collection unit 40 includes a nozzle tip discarder 41 provided at the stopping position 113a and used to remove and discard the disposable nozzle tip 14 mounted on the nozzle 95a-95e that has stopped at the stopping position 113a (the removal and discard of the nozzle tip is hereinafter termed "nozzle tip discarding process"). The reaction vessel collection unit 40 also includes a reaction vessel collection line 43 provided at the stopping position 115a and used to collect the reaction vessel 2 retained by the opening (e.g. in FIG. 6, opening 115) that has stopped at the stopping position 115a (the collection is hereinafter termed the reaction vessel collection process). The stopping position 114a is a standby position for an opening not retaining a specimen container holder 3.

The reaction vessel collection line 43 includes a belt conveyor 26 that carries the reaction vessel 2 within a specimen container holder 3, from the transport mechanism 90A to the extract collection unit 54, and a specimen container holder positioning partition 26a that appropriately positions the specimen container holder 3 with respect to the belt conveyor 26 and suppresses slipping of the holder on the conveyor 26. After stopping a desired opening (e.g. in FIG. 6, the opening 115) at the stopping position 115a by rotating the turntable 91A of the transport mechanism 90A, the processing system actuates the belt conveyor 26 to collect from that opening the specimen container holder 3 containing the reaction vessel 2, and a part of the vessel 2 is carried to the extract collection unit 54 not shown, via the filter discarder 53 (also not shown). At the filter discarder 53, the pressurized filtering vessel section 2b of the reaction vessel 2 is removed and discarded and the remaining collection vessel section 2a is carried to the extract collection unit 54.

The extract (target constituents) inside the collection vessel section 2a which has been collected into the extract collection unit 54, that is, the supernatant that has been collected after protein precipitation is sent to a process site 55 for purification and measurement. The supernatant is, if needed, optionally dried up and redissolved using a dissolving solution for reduction in the amount of liquid and for concentration of the desired constituents, and further analyzed with a liquid chromatograph-mass spectrometer (LCMS) or the like. Thus, the desired constituents are separated/purified and detected, and identification and quantitative analysis of the constituents are conducted.

The total control unit 88, intended for operational control of the entire specimen processing system, includes input means, storage means, display means, and more (none of them shown). Upon setup parameters for the system constituent elements being entered by the input means, the total control unit 88 controls operation of each system element in accordance with software stored within the storage means, and preprocesses the target specimen. In addition, if an unusual situation occurs in either of the processing units 10, 20, 30, 250, 40, 50, 62, 63, 72, the total control unit 88 immediately suspends the operation of the entire specimen processing system and presents an alarm to a display device not shown.

Processing sequences in the specimen processing system of the present embodiment are next described below. The description assumes that during a start of preprocessing, the openings 101-115 are present at the respective initial positions shown in FIG. 6.

First, an operator loads a specimen container 1 containing the target specimen into a specimen container holder 3, stores this specimen container holder into a specimen container rack 4, and sets this rack on the specimen container supply unit 62. Additionally, the operator loads a reaction vessel 2 into another specimen container holder 3, stores this specimen container holder into another specimen container rack 4, and sets this rack on the reaction vessel supply unit 63. Under this state, the operator assigns a preprocessing start-up instruction using the input means (not shown) of the total control unit 88.
(Sequence 1)

The nozzle 295a moves to the stopping position 101a. At this time, the nozzles 295b, 295c, 295d, 295e move to the stopping positions 104a, 107a, 110a, 113a, respectively. Under this state, the processes described below are simultaneously conducted at the processing units 10, 20, 30, 250, 40.

At the dispensing unit 10, a nozzle tip is mounted at the stopping position 101a, a specimen container is supplied to the opening 102 at the stopping position 102a, and a reaction vessel is supplied to the opening 103 at the stopping position 103a. The three processes are conducted at the same time.

At the hemolyzing unit 20, the specimen container is collected from the opening 105 at the stopping position 105a, and a hemolyzing solution is injected as a first reagent into the reaction vessel 2 retained by the opening 106 at the stopping position 106a. The nozzle 295b at the stopping position 104a merely moves in accordance with the nozzle 295a.

At the protein precipitating unit 30, a protein-precipitating solution is injected as a second reagent into the reaction vessel 2 retained by the opening 109 at the stopping position 109a. The nozzle 295c at the stopping position 107a merely moves in accordance with the nozzle 295a.

At the pressurizing unit 250, the pressurizing mechanism 52A pressurizes the reaction vessel 2 retained by the opening 112 at the stopping position 112a. The pressurizing mechanism 52A immediately retreats from the transport line after the pressurization.

At the reaction vessel collection unit 40, the nozzle tip 14 is removed from the nozzle 295d at the stopping position 113a and discarded, and the reaction vessel is collected from the opening 115 at the stopping position 115a.
(Sequence 2)

The nozzle 295a moves to the stopping position 102a. At this time, the nozzles 295b, 295c, 295d, 295e move to the stopping positions 105a, 108a, 111a, 114a, respectively. Under this state, the processes described below are simultaneously conducted at the processing units 10, 20, 30, 250, 40.

At the dispensing unit 10, the contents of the specimen container 1 retained by the opening 102 at the stopping position 102a are mixed and suctioned.

At the hemolyzing unit 20, the nozzle 295b at the stopping position 105a merely moves in accordance with the nozzle 295a.

At the protein precipitating unit 30, the nozzle 295c at the stopping position 108a merely moves in accordance with the nozzle 295a.

At the pressurizing unit 250, the nozzle 295d at the stopping position 111a merely moves in accordance with the nozzle 295a.

At the reaction vessel collection unit 40, the nozzle 295e at the stopping position 114a merely moves in accordance with the nozzle 295a.

(Sequence 3)

The nozzle 295a moves to the stopping position 103a. At this time, the nozzles 295b, 295c, 295d, 295e move to the stopping positions 106a, 109a, 112a, 115a, respectively. Under this state, the processes described below are simultaneously conducted at the processing units 10, 20, 30, 250, 40.

At the dispensing unit 10, the target specimen is discharged into and then mixed in the reaction vessel 2 retained by the opening 103 at the stopping position 103a. At the hemolyzing unit 20, the contents of the reaction vessel 2 retained by the opening 106 at the stopping position 106a are mixed.

At the protein precipitating unit 30, the contents of the reaction vessel 2 retained by the opening 109 at the stopping position 109a are mixed.

At the pressurizing unit 250, the nozzle 295d at the stopping position 112a merely moves in accordance with the nozzle 295a.

At the reaction vessel collection unit 40, the nozzle 295e at the stopping position 115a merely moves in accordance with the nozzle 295a.

(Sequence 4)

The nozzle 295a moves to the stopping position 104a. At this time, the nozzles 295b, 295c, 295d, 295e move to the stopping positions 107a, 110a, 113a, 101a, respectively. In addition, at the same time that the nozzles 295a-295e move, the openings 101-115 move through three pitches counterclockwise. That is, the openings 113-115 move to the stopping positions 101a-103a, respectively, and the openings 101-112 move to the stopping positions 104a-115a, respectively.

At the state of layout after sequence 4, processes equivalent to the sequences 1 to 4 are repeated by regarding "nozzle 295e" as "nozzle 295a" and "openings 113-115" as "openings 101-103", and also by regarding the other parts "nozzles 295a-295d" and the "openings 101-112" correspondingly. Repeating the processes equivalent to the sequences 1 to 4 in such a manner allows each process to be continuously conducted upon the target specimens.

Substantially same beneficial effects as that of the first embodiment can also be obtained in the present (second) embodiment having the above configuration.

Third Embodiment

A third embodiment of the present invention is characterized in that a dispensing/mixing mechanism that dispenses specimens and mixes reaction solutions is not present on the same axis as that of a turntable having reaction vessels arranged thereon, and in that each of the reaction vessels is such that a filtering vessel section and a solid-phase extraction section are integrated into one unit.

Figure 7:
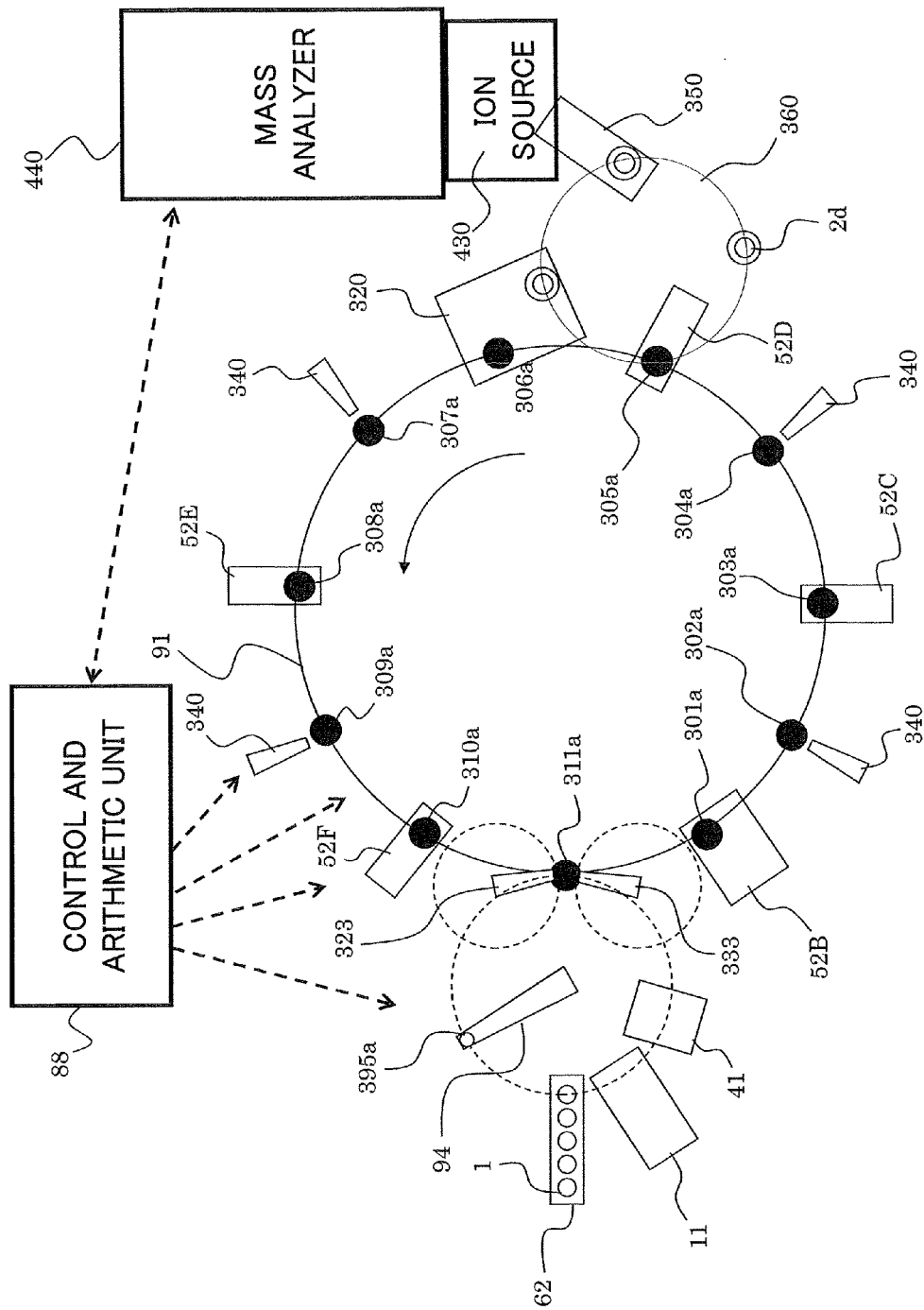
FIG. 7 is a plan view schematically showing a total specimen processing system configuration according to a third embodiment of the present invention.

FIG. 7 shows a schematic of a specimen processing system for measuring the quantity of immunosuppressant drug in whole blood by a mass spectrometer, which the system processes steps from hemolyzation, deproteinization, solid-phase extraction, to mass spectrometry, fully automatically.

The dispensing/mixing mechanism 94 in the present embodiment is characterized in that the mechanism 94 is positioned on an outer circumference of the turntable 91. On the outer circumference of the turntable 91, various processing mechanisms are arranged at stopping positions 301a to 310a and 311a, as in the first and second embodiments.

As in the first and second embodiments, the turntable 91 rotationally moves counterclockwise in units of one stopping position according to each process step. Orders of the processing steps executed, and an operational outline of the processing mechanisms, at each stopping position, are listed in FIG. 10.

Although the dispensing/mixing mechanism 94 is positioned on the outer circumference of the turntable 91, a path traced by a disposable nozzle tip 14 mounted at a distal end of a nozzle 395a will intersect a path of a reaction vessel present on the turntable 91 at one stopping position, 311a, provided on a path of the turntable 91. At the stopping position 311a (the intersection), after a specimen has been dispensed using one disposable nozzle tip for one reaction vessel, a reaction solution that is a first reagent is injected at the stopping position 311a using a first reagent dispensing mechanism 323, and then mixed by suctioning and discharging with the same disposable nozzle tip as that mentioned above. After this, another reaction solution that is a second reagent is injected at the stopping position 311a using a second reagent dispensing mechanism 333, and then mixed by suctioning and discharging with the same disposable nozzle tip as used above. Briefly, the dispensing/mixing mechanism 94 uses one disposable nozzle tip to execute three steps, namely, dispensing the specimen to the reaction vessel, mixing the first reaction solution, and mixing the second reaction solution.

Since specimen dispensing and the mixing operations in the steps relating to a plurality of reaction solutions are conducted in such way using the disposable nozzle tip 14, it enables to avoid the necessity to be equipped with a mechanism for specimen-dispensing pipette cleaning, a mixing mechanism, and a cleaning mechanism for mixing parts, upon whole-blood processing. This enables to provide a configuration such that preprocesses specimens, which separation and extraction are to be conducted by using reaction vessels arranged on a caterpillar track, continuously at random time intervals, and also enables to reduce consumption costs of disposable parts. At the same time, low-carryover separation/extraction or preprocessing for separation/extraction can be executed for the target constituents.

A nozzle tip discarder 41, a nozzle tip supply unit 11, and a specimen supply unit 62 are arranged on a path of the dispensing/mixing mechanism 94. In addition, the mechanism 323 for dispensing the first reagent (hemolyzing solution), and the mechanism 333 for dispensing the second reagent (protein-precipitating solution) are arranged on the same axis as, or an axis different from, that of the dispensing/mixing mechanism 94. FIG. 7 shows an example of layout on different axes. A mechanism for dispensing an internal standard liquid substance (or the like) for quantitative analysis by mass spectrometry may be further disposed if required. Furthermore, the hemolyzing solution, the protein-precipitating solution, and the internal standard liquid substance or the like may be dispensed using either a dispenser scheme having the dispensing mechanism connected directly to reagent containers, or a scheme in which reagent containers are arranged separately from the dispensing mechanism such that the dispensing mechanism can discharge a reagent towards a solution to be processed by reaction after suctioning the reagent from a reagent container.

Figure 11:
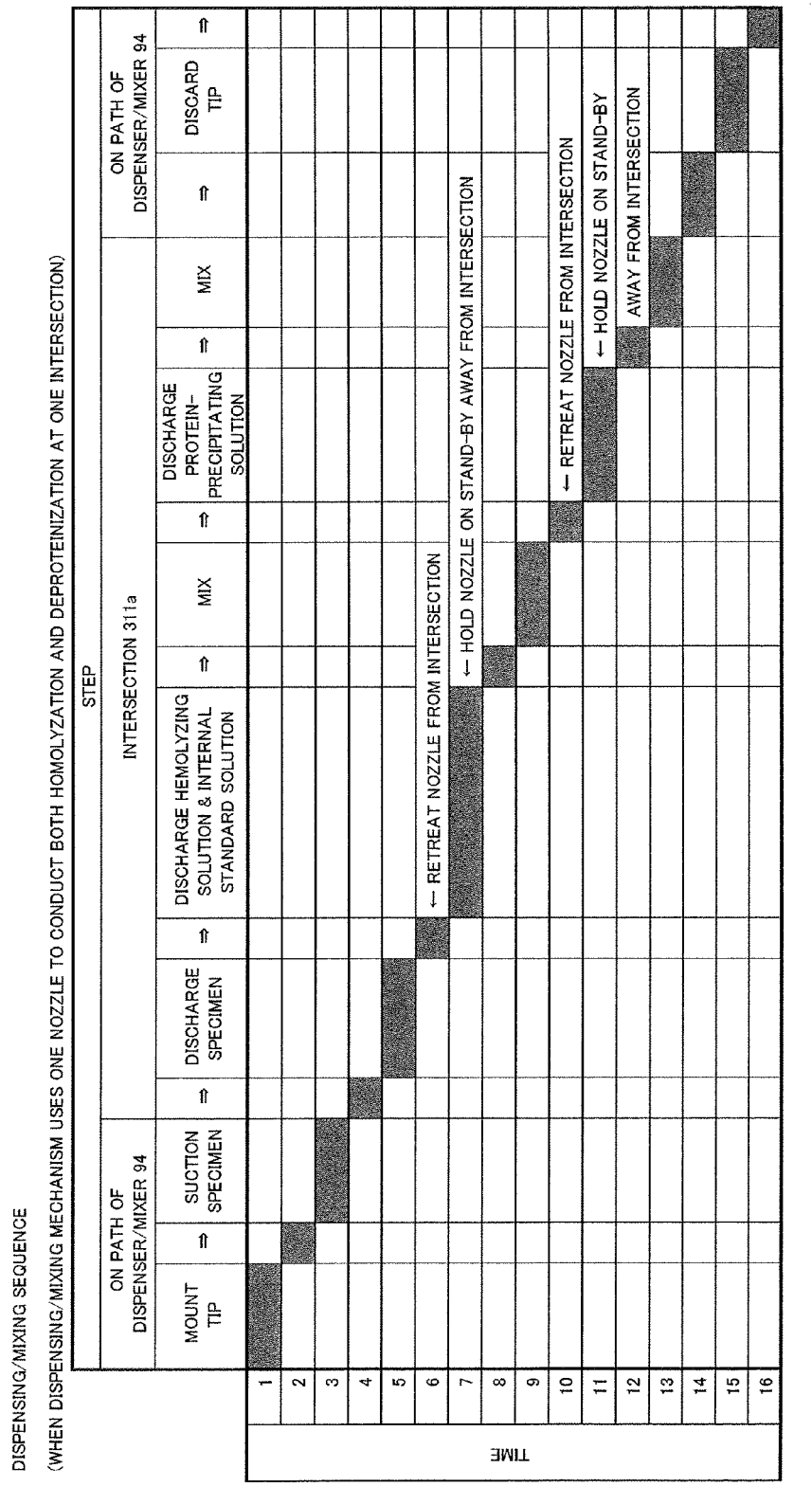
FIG. 11 is a timetable representing an operational sequence of a dispensing/mixing mechanism in the third embodiment of the present invention.

Operation of various mechanisms involved with the dispensing/mixing mechanism 94 is described below. A timetable of each step is shown in FIG. 11.

First, the dispensing/mixing mechanism 94 mounts a disposable nozzle tip 14 on the nozzle 395a, at the nozzle tip supply unit 11.

Next, the dispensing/mixing mechanism 94 moves to the specimen supply unit 62 in an orbital path and suctions a specimen.

Next, the dispensing/mixing mechanism 94 moves in an orbital path to the stopping position 311a at which the mechanism intersects the turntable 91, and discharges the specimen into a reaction vessel 2 present at that position.

Next if necessary, the dispensing/mixing mechanism 94 orbitally retreats from the stopping position 311a, the intersection with the turntable 91.

Next, the first reagent (hemolyzing solution) dispensing mechanism 323 discharges a necessary amount of hemolyzing solution into the reaction vessel, and then retreats from the stopping position 311a, the intersection with the turntable 91.

After the retreat, the dispensing/mixing mechanism 94 orbitally moves to the stopping position 311a, the intersection with the turntable 91, and mixes the reaction solution within the reaction vessel 2 positioned there.

Next if necessary, the dispensing/mixing mechanism 94 orbitally retreats from the stopping position 311a, the intersection with the turntable 91.

Next, the second reagent (protein-precipitating solution) dispensing mechanism 333 discharges a necessary amount of protein-precipitating solution into the reaction vessel 2, and then retreats from the stopping position 311a, the intersection with the turntable 91.

Next, the dispensing/mixing mechanism 94 orbitally moves to the stopping position 311a, the intersection with the turntable 91, and mixes the reaction solution within the reaction vessel 2 positioned there.

Next, the dispensing/mixing mechanism 94 orbitally moves to the nozzle tip discarder, removes the used disposable nozzle tip 14 from the nozzle 395a, and discards the nozzle tip.

These are the operation conducted when the paths of dispensing/mixing mechanism 94 and the turntable 91 intersect at one position. During this process, the turntable 91 maintains a stationary state, and upon completion of the above operational sequence, the turntable 91 moves through a distance equivalent to one pitch. Thus, the reaction vessel disposed at the intersection of the paths of the dispensing/mixing mechanism and the turntable 91 moves to the stopping position 301a, and is then subjected to pressurization for filtering. At the same time, another reaction vessel 2 at the stopping position 310a moves to and stops at the intersection 311a of the paths of the dispensing/mixing mechanism 94 and the turntable 91. The same sequence as described above is repeated for the reaction vessel 2 newly positioned at the intersection 311a.

If an internal-standard liquid substance dispensing mechanism is needed to be provided, process steps for suctioning an internal standard liquid substance and for discharging the internal standard liquid substance are suitably conducted between the specimen discharging process step and the hemolyzing solution discharging process step.

Figure 15:
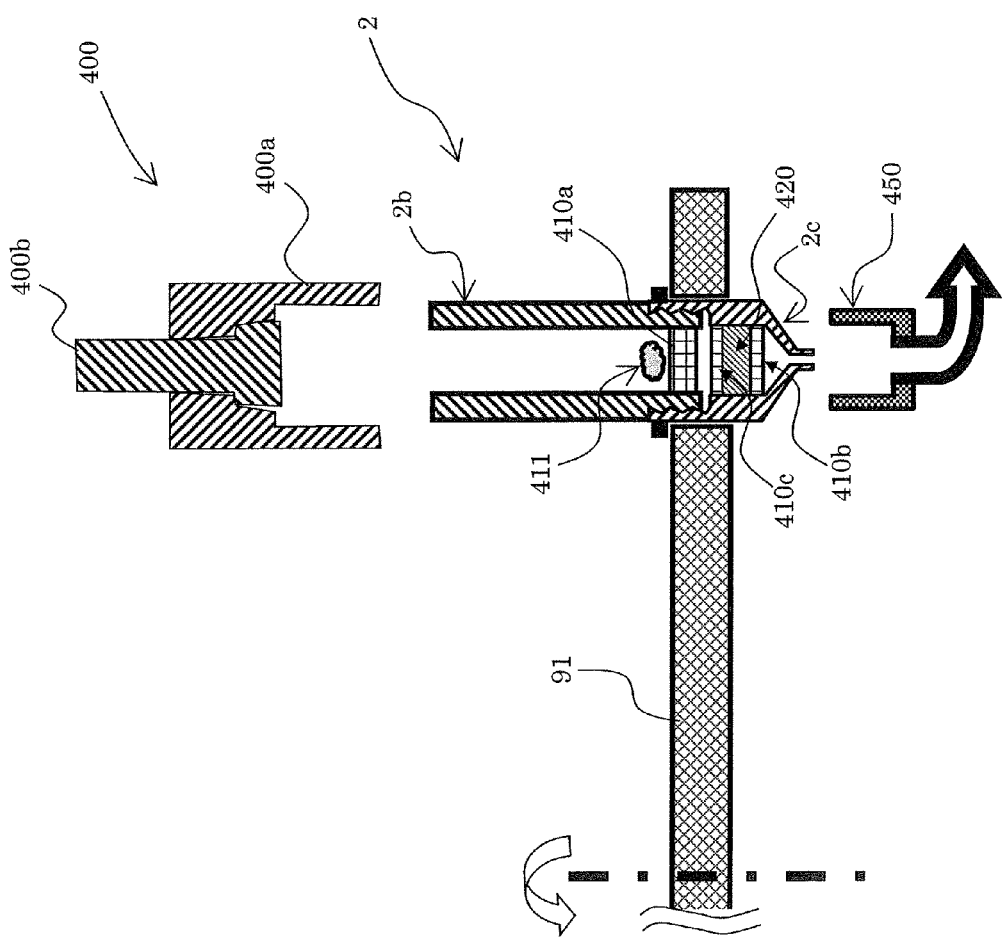
FIG. 15 is a cross-sectional view showing a pressurizer, reaction vessel, and collection vessel section of either the third, fourth, or fifth embodiment of the present invention.
Figure 16:
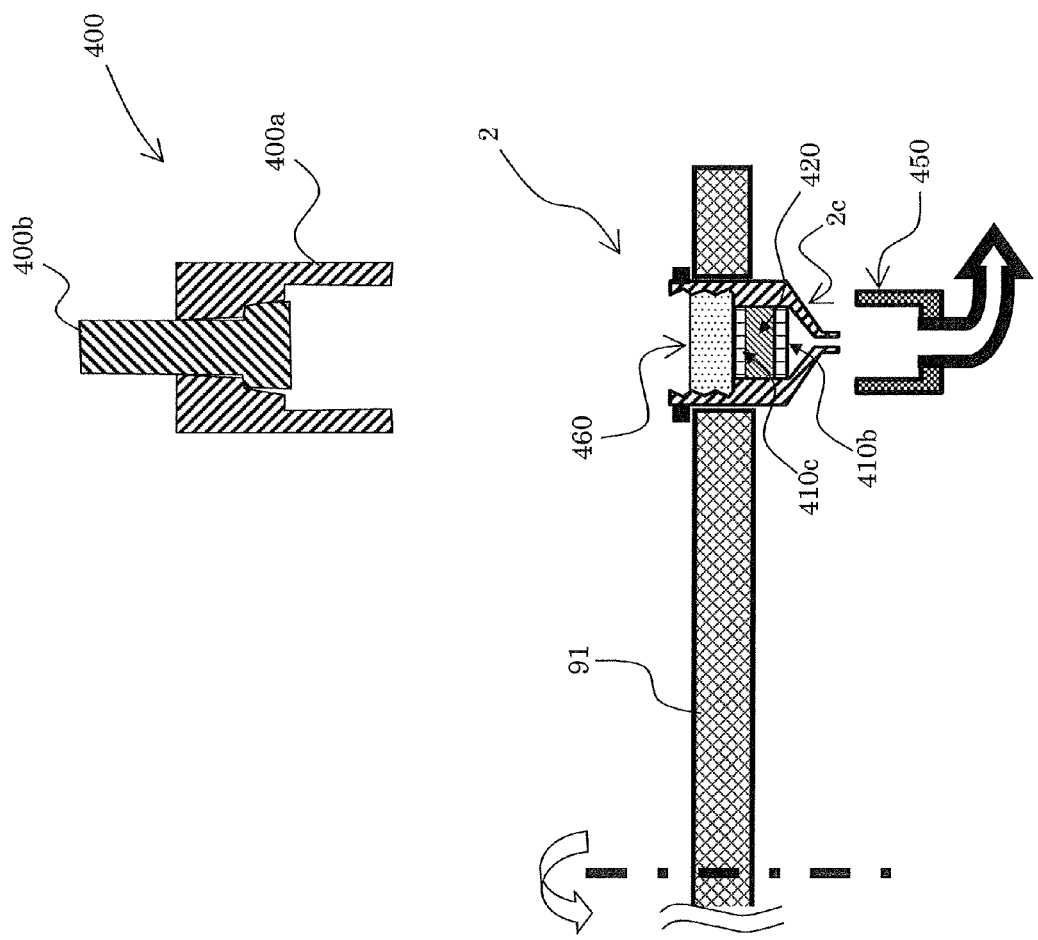
FIG. 16 is a diagram representing a relationship between the pressurizer and reaction vessel during washing at a stopping position.
Figure 17:
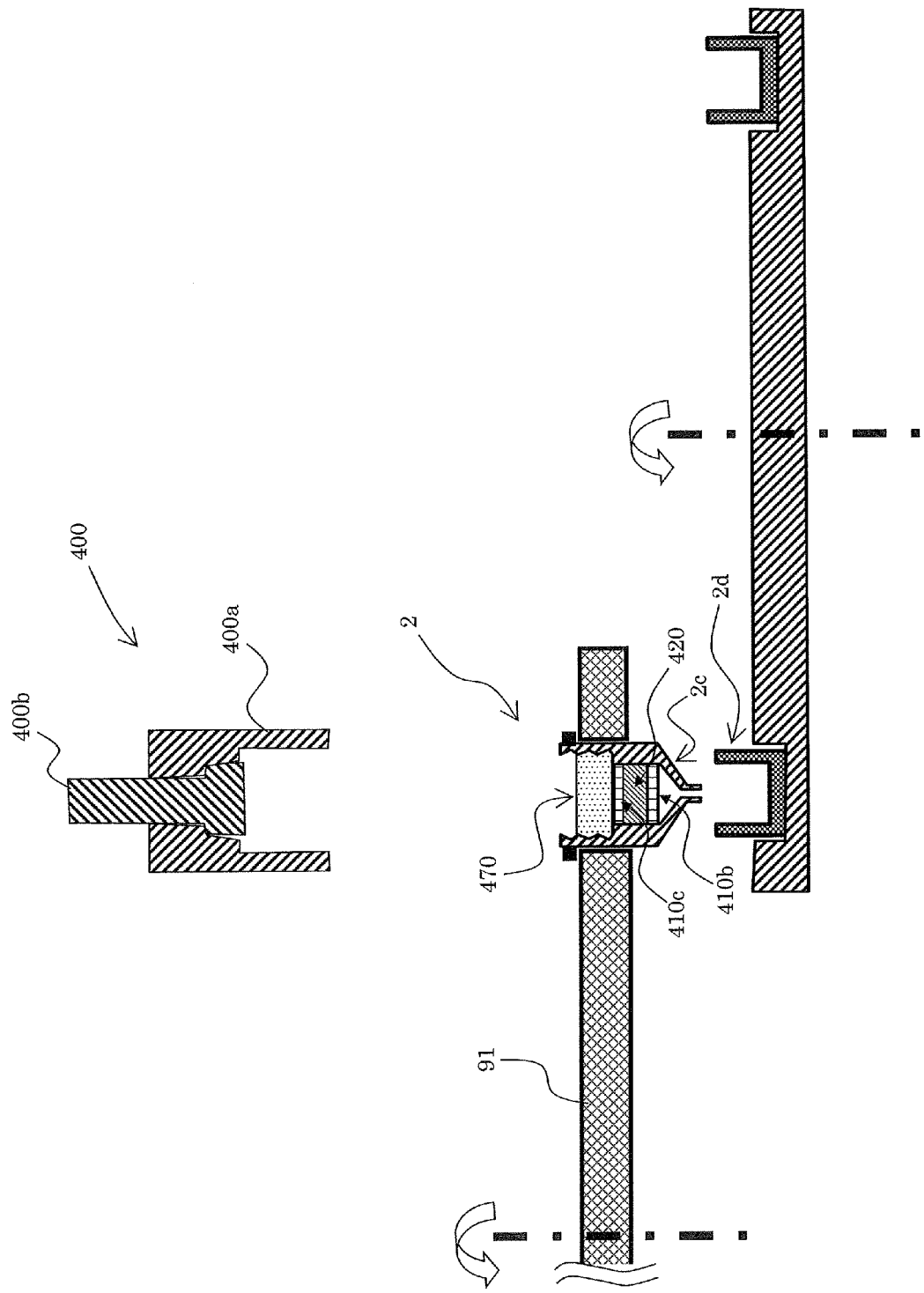
FIG. 17 is a diagram representing a relationship between the pressurizer, reaction vessel, extract cup, and cup table, during elution at the stopping position.

Pressurizing mechanisms 52C to 52F and a pressurizing mechanism/filter removal mechanism 52B are both equipped with a pressurizer 400 that includes a pressurizer holder 400a and a pressurizing syringe 400b, which are shown in FIGS. 15 to 17.

As shown in FIG. 15, each reaction vessel 2 includes a filtering vessel section 2b having a filter 410a at bottom, and a solid-phase extraction section 2c containing a solid-phase extraction packing sorbent 420 for directly receiving a filtrate that has passed through the filter 410a. The solid-phase extraction packing sorbent 420 is housed in a required position between an upper filter 410c and a lower filter 410b.

Under a no-pressure state, various solutions accommodated in the filtering vessel section 2b, and the specimen to be processed pass through the filter 410a very slowly, and in effect, they stay in the filtering vessel section 2b. Upon the filtering vessel section 2b being internally pressurized, desired constituents pass through the filter 410a and the various solutions and the specimen enter the solid-phase extraction section 2c.

FIG. 15 represents a positional relationship of the pressurizer 400 and the reaction vessel 2 located at the stopping positions 308a, 310a, or 301a. However, no protein precipitate 411 is present at the stopping positions 308a, 310a. Upon pressurization at the three stopping positions, the various solutions and the specimen pass through the filter 410a and enter the solid-phase extraction section 2c. Constituents that do not become adsorbed onto the solid-phase extraction packing sorbent 420 pass through the solid-phase extraction section 2c and are guided into a waste liquid line 450 provided below the extraction section 2c.

At the stopping position 301a, since a specimen solution is pressurized, the desired constituents become adsorbed onto the solid-phase extraction packing sorbent 420. The pressurization at the stopping position 301a is conducted by the pressurizing mechanism/filter removal mechanism 52B. After the pressurization, the filtering vessel section 2b laden with precipitated impurities is removed from the reaction vessel 2 by the pressurizing mechanism/filter removal mechanism 52B and discarded. As a result, the solid-phase extraction section 2c of the reaction vessel 2 is left and then advances to the next stopping position, 302a.

FIG. 16 represents a positional relationship of the pressurizer 400 and the reaction vessel 2 during washing at the stopping position 303a. Upon pressurization in this positional relationship, impurities, exclusive of the desired constituents adsorbed onto the solid-phase extraction packing sorbent 420, are washed away and guided into the waste liquid pine 450.

FIG. 17 represents a positional relationship of the pressurizer 400 during elution, the reaction vessel 2, an extract cup 2d, and a cup table 360, at the stopping position 305a. A plurality of extract cups 2d, each of which is a receptacle for receiving a solid-phase extracted solution (extract), are arranged on the cup table 360. Pressurization in this positional relationship desorbs the desired constituents from the solid-phase extraction packing sorbent 420, and elutes the constituents into the extract contained in the extract cup 2d.

The extract that has been stored into the extract cup 2d is carried to a neighboring region of an ion source 430 by a rotational movement of the cup table 360, and then loaded into the ion source 430 by a preprocessed specimen introducing mechanism 350. The preprocessed specimen introducing mechanism 350 is based on an auto-sampler used in a normal type of liquid chromatographic assay method. After being ionized by the ion source 430, the specimen is measured quantitatively, and measured data is sent to a total control unit 88.

As mentioned in the description of the present embodiment, the reaction vessel 2, despite the filtering vessel section and the solid-phase extraction section being integrally connected to each other, is constructed so as to be removable from the solid-phase extraction section after filtering. During filtering, therefore, the filtrate can be sent to the solid-phase extraction section automatically without loss and efficiently. In addition, this structure enables to remove protein precipitate rapidly and readily after filtering. The protein precipitate, if left in the vessel, can interfere with measurements because impurity would be dissolved from the precipitate during washing and eluting process steps of solid-phase extraction.

Fourth Embodiment

Figure 8:
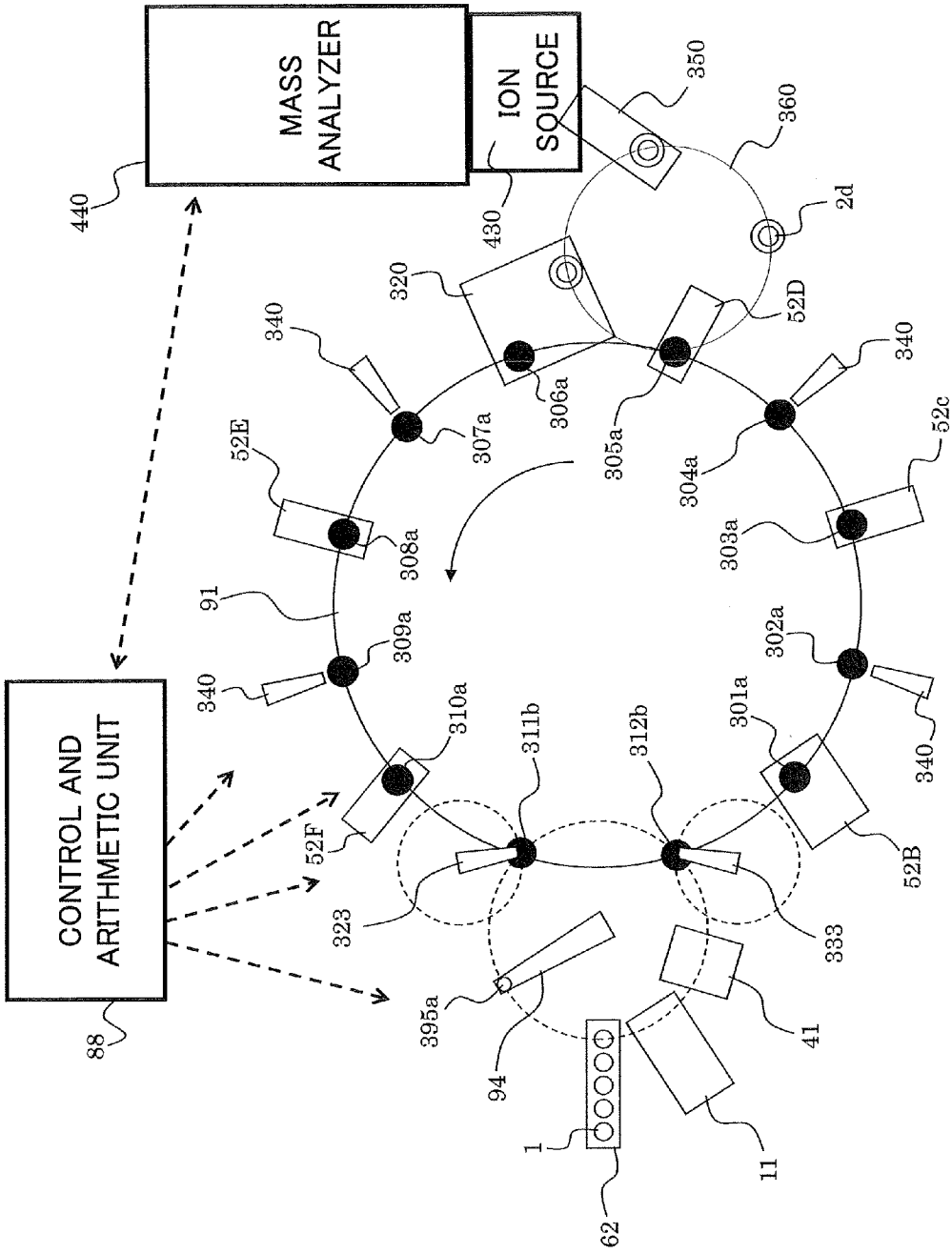
FIG. 8 is a plan view schematically showing a total specimen processing system configuration according to a fourth embodiment of the present invention.

A fourth embodiment, shown in FIG. 8, is characterized in that, as in the third embodiment, a dispensing/mixing mechanism that dispenses specimens and mixes reaction solutions is not present on the same axis as that of a turntable having reaction vessels arranged thereon. A difference from the third embodiment is that a path of a nozzle 395a on the dispensing/mixing mechanism 94 and a path of a reaction vessel 2 on the turntable 91 intersect at two positions. At the two intersections, a specimen, a hemolyzing solution, and a protein-precipitating solution are dispensed into the reaction vessel. Reaction solutions are also mixed at the intersections.

Operational differences from the third embodiment are mainly described below.

A nozzle tip discarder, a nozzle tip supply unit, and a specimen supply unit are arranged on the path of the dispensing/mixing mechanism 94. In addition, a mechanism for dispensing the hemolyzing solution, and a mechanism for dispensing the protein-precipitating solution are arranged on the same axis as, or an axis different from, that of the dispensing/mixing mechanism 94. FIG. 8 shows an example of layout on a different axis. A mechanism for dispensing an internal standard liquid substance or the like may be further disposed if required. Furthermore, reagents such as the hemolyzing solution, protein-precipitating solution, and internal standard liquid substance or the like, may be dispensed using either a dispenser scheme having the dispensing mechanism connected directly to reagent containers, or a scheme in which reagent containers are arranged separately from the dispensing mechanism so that the dispensing mechanism can discharge a reagent into a solution to be processed by reaction after suctioning the reagent from a reagent container.

When two intersections exist, a first intersection 311b at an upstream side of rotational movement of the turntable 91 is desirable, rather than a second intersection 312b at a downstream side of rotational movement, to be a position that a process of an upstream side of successive processes is executed. For whole-blood processing, for example, hemolyzation and protein precipitation are desirably conducted at the first intersection and the second intersection, respectively. However, since the hemolyzation process and the protein precipitation process are each constituted by various dispensing operations and mixing operations, switching from the first intersection to the second intersection may take place at any operation step, if an order of execution of the successive operations is duly followed.

Figure 12:
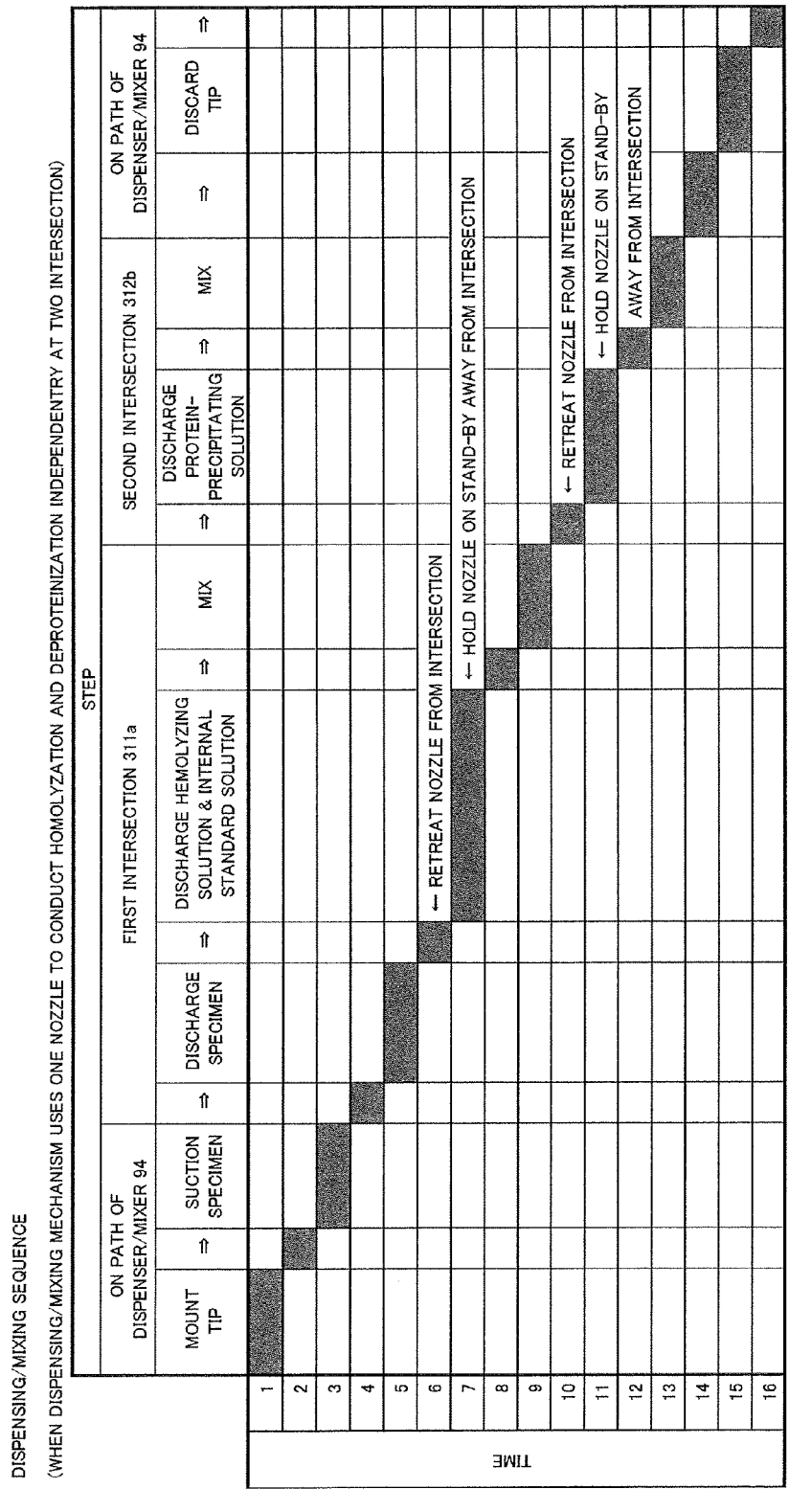
FIG. 12 is a timetable representing an operational sequence of a dispensing/mixing mechanism in the fourth embodiment of the present invention.

The embodiment shown in FIG. 8 applies to a case in which, after the hemolyzation at the first intersection, protein precipitation is conducted at the second intersection. Specific operation of various related mechanisms is described below. In addition, a timetable of process steps is shown in FIG. 12.

First, the dispensing/mixing mechanism 94 mounts a disposable nozzle tip 14 on the nozzle 395a, at the nozzle tip supply unit 11.

Next, the dispensing/mixing mechanism 94 moves to the specimen supply unit 62 in an orbital path and suctions a specimen.

Next, the dispensing/mixing mechanism 94 moves in an orbital path to the first intersection 311b with the turntable 91, and discharges the specimen into a reaction vessel 2 present at that position.

Next, if necessary, the dispensing/mixing mechanism 94 orbitally retreats from the first intersection 311b with the turntable 91.

Next, the first reagent (hemolyzing solution) dispensing mechanism 323 discharges a necessary amount of hemolyzing solution into the reaction vessel 2 at the first intersection 311b with the turntable 91, and then retreats from the first intersection 311b.

After the retreat, the dispensing/mixing mechanism 94 orbitally moves to the first intersection 311b that intersects with the turntable 91, and mixes the reaction solution within the reaction vessel 2 positioned there.

Next, if necessary, the dispensing/mixing mechanism 94 orbitally retreats from the first intersection 311b with the turntable 91.

Next, the turntable 91 moves through one stopping position. The reaction vessel which the hemolyzing process was conducted moves to the second intersection 312b, and another reaction vessel 2 that stayed at the stopping position 310a in the previous step moves to the first intersection 311b.

Next, the second reagent (protein-precipitating solution) dispensing mechanism 333 discharges a necessary amount of protein-precipitating solution into the reaction vessel that has moved to the second intersection 312b with the turntable, and then retreats from the intersection 312b.

Next, the dispensing/mixing mechanism 94 orbitally moves to the second intersection 312b with the turntable 91, and mixes the reaction solution within the reaction vessel 2 positioned there.

Next, the dispensing/mixing mechanism 94 orbitally moves to the nozzle tip discarder 41, removes the used disposable nozzle tip 14 from the nozzle 395a, and discards the nozzle tip.

Next, the dispensing/mixing mechanism 94 mounts another disposable nozzle tip 14 on the nozzle 395a, at the nozzle tip supply unit 11, and after suctioning a specimen solution from another specimen container 1, repeats the above-described successive hemolyzing operations for the reaction vessel 2 placed at the first intersection 311b.

If an internal-standard liquid substance dispensing mechanism is needed to be provided, process phases for suctioning an internal standard liquid substance and discharging the internal standard liquid substance into the reaction vessel are suitably provided between the specimen discharging process phase and hemolyzing solution discharging process phase at the intersection 311b.

Fifth Embodiment

Figure 9:
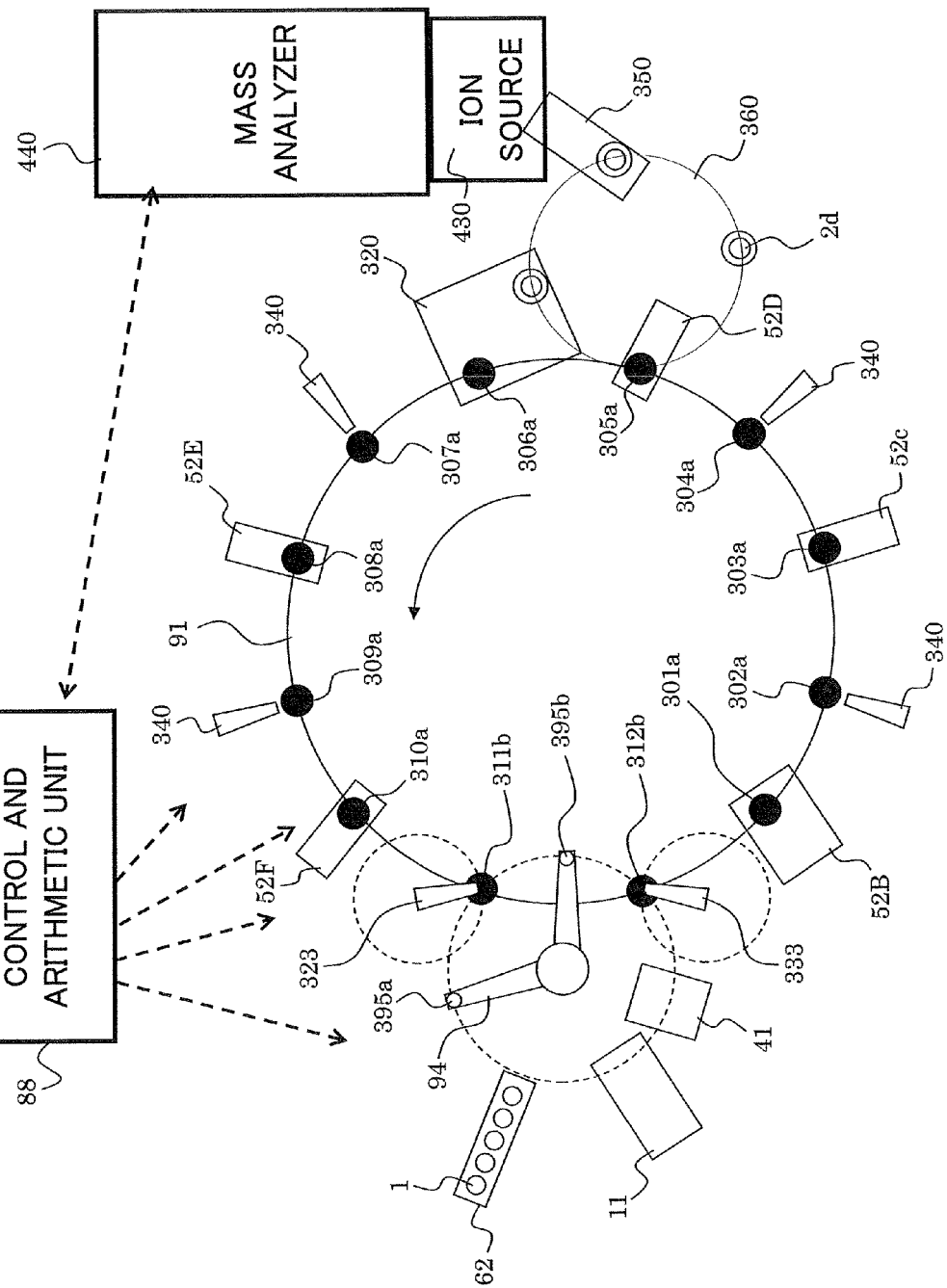
FIG. 9 is a plan view schematically showing a total specimen processing system configuration according to a fifth embodiment of the present invention.
Figure 13:
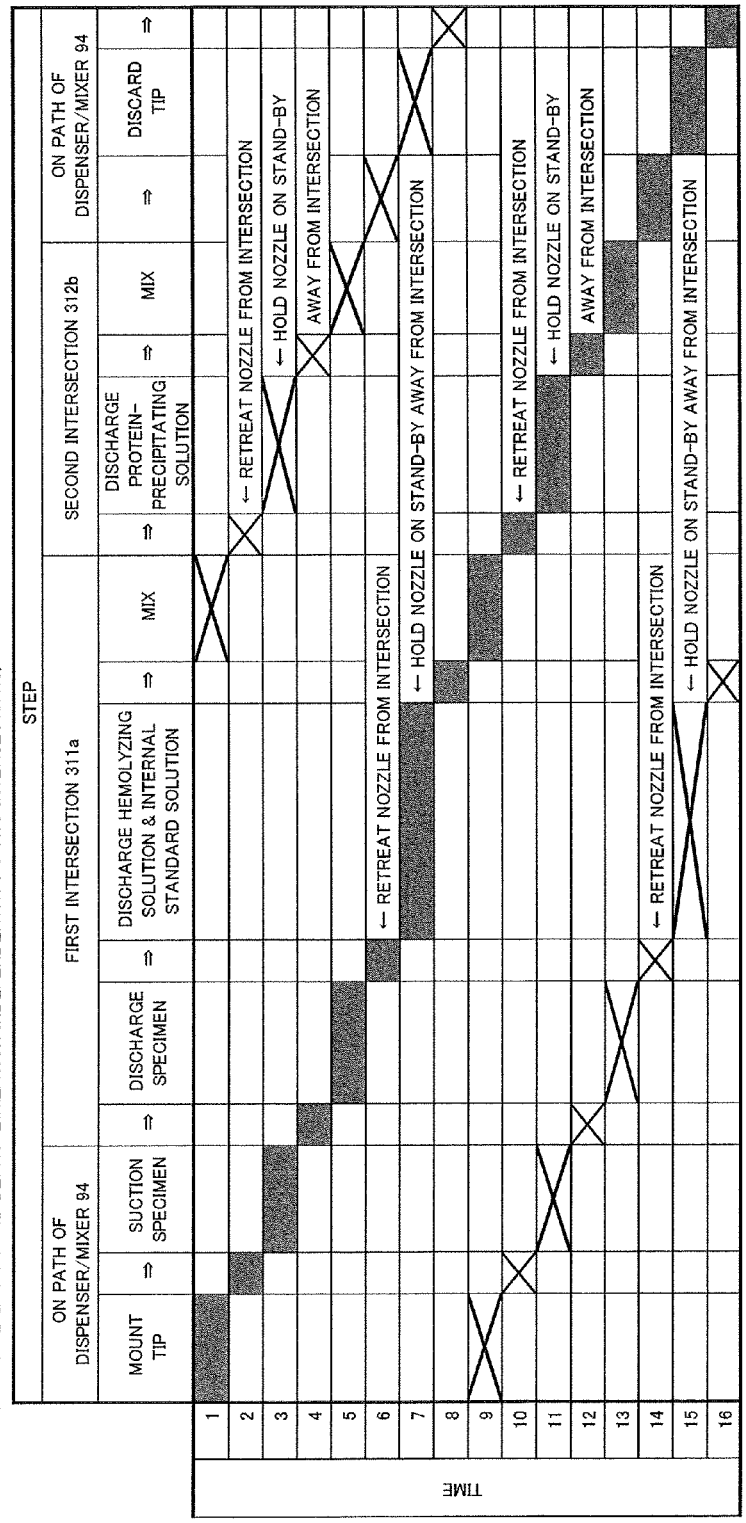
FIG. 13 is a timetable representing an operational sequence of a dispensing/mixing mechanism in the fifth embodiment of the present invention.

A fifth embodiment, shown in FIG. 9, is characterized in that as in the third and fourth embodiments, a dispensing/mixing mechanism that dispenses specimens and mixes reaction solutions is not present on the same axis as that of a turntable having reaction vessels arranged thereon. The fifth embodiment is also characterized in that as in the fourth embodiment, a path of a nozzle 395a on the dispensing/mixing mechanism 94 and a path of a reaction vessel 2 on the turntable 91 intersect at two positions. In addition, in order to enhance working efficiency at the two intersections, the dispensing/mixing mechanism 94 has two nozzles, 395a and 395b, that operate independently of each other on the same axis, and is thus able to conduct concurrent processing upon the reaction vessels 2 positioned at the intersections 311b and 312b on the turntable 91. A timetable of related process steps is shown in FIG. 13. Assigning this concurrent processing allows a preprocessing system to be capable of executing separation and extraction of immunosuppressant drug constituents from whole blood rapidly, with short TAT, at a low carry-over rate, and in a state that preprocessing of specimens can be randomly, continuously started.

While a specimen processing system targeted for biological specimens (whole-blood specimens) has been described in the present embodiment, the present invention is not limited to the embodiment and obviously can also be applied to specimen processing systems used in a wide range of fields related to environments, foodstuffs, and more.

DESCRIPTION OF REFERENCE NUMBERS

1 Specimen container
2 Reaction vessel
2a Collection vessel section
2b Filtering vessel section
2c Solid-phase extraction section
2d Extract cup
3 Specimen container holder
4 Specimen container rack
10 Dispensing unit
11 Nozzle tip supply unit
12 Specimen container supply line
13 Reaction vessel supply line
14 Nozzle tip
15 Nozzle tip rack
16 Nozzle tip rack moving mechanism
17 Belt conveyor
17a Specimen container holder positioning partition
18 Belt conveyor
18a Specimen container holder positioning partition
20 Hemolyzing unit
22 Specimen container collection line
23 First reagent (hemolyzing solution) injector
24 Belt conveyor
24a Specimen container holder positioning partition
25 Solution/solvent tank
30 Protein precipitating unit
33 Second reagent (protein-precipitating solution) injector
34 Solution/solvent tank
40 Reaction vessel collection unit
41 Nozzle tip discarder
43 Reaction solution collection line
50 Precipitate removing unit
51 Transport mechanism
52, 52A, 52C, 52D, 52D, 52E, 52F Pressurizers
52B Pressurizing mechanism/filter removal mechanism
53 Filter discarder
54 Extract collection unit
55 Purifying/measuring step
62 Specimen container supply unit
63 Reaction vessel supply unit
72 Specimen container collection unit
88 Total control unit
90, 90A Transport mechanisms
91, 91A Turntables
92 Specimen container holder-retaining member
93 Specimen container holder anti-drop guard
94, 294 Dispensing/mixing mechanisms
95, 295 Bases
95a-95d, 295a-295e Nozzles
96 Suctioning/discharging mechanism
97 Rotational driving mechanism
98 Driving mechanism
101-115 Openings
101a-115a Stopping positions
250 Pressurizing unit
301a, 303a, 305a, 308a, 310a Stopping positions (Pressurization for solid-phase extraction)
302a Stopping position (Washing agent dispensing for solid-phase extraction)
304a Stopping position (Eluting solution dispensing for solid-phase extraction)
306a Stopping position (Reaction vessel mounting/collection for solid-phase extraction)
307a Stopping position (Conditioning liquid-A dispensing for solid-phase extraction)
309a Stopping position (Conditioning liquid-B dispensing for solid-phase extraction)
311a Stopping position (Specimen dispensing, first reagent dispensing, reaction solution mixing, and second reagent dispensing)
311b Stopping position (Specimen dispensing, first reagent dispensing, and reaction solution mixing)
312b Stopping position (Second reagent dispensing and reaction solution mixing)
320 Reaction vessel mounting/collecting mechanism
323 First reagent (hemolyzing solution) dispensing mechanism
333 Second reagent (protein-precipitating solution) dispensing mechanism
340 Dispensing mechanism
350 Preprocessed specimen introducing mechanism preprocessing
360 Cup table
395a, 395b Nozzles
400 Pressurizer
400a Pressurizer holder
400b Pressurizing syringe
400c Pressurizer base
410a, 410b, 410c Filters
411 Protein precipitate
420 Solid-phase extraction packing sorbent
430 Ion source
440 Mass spectrometer
450 Waste liquid line
460 Washing agent
470 Eluting solution

The invention claimed is:

1. A specimen processing system for separating, purifying, or filtering specimens, the system comprising:
a turntable rotatably driven to transport one or more reaction vessels used for separating and extracting desired substances from a specimen to be processed,
a suctioning and discharging mechanism rotatably driven that dispenses the specimen from a specimen container supplied to the processing system into the one or more reaction vessels; and
a cup table rotatably driven to transport a plurality of cups, which are receptacles for receiving a solution reacted within the one or more reaction vessels,
wherein the cup table and the turntable do not rotate around the same axis,
the suctioning and discharging mechanism includes a base, and, at a plurality of different points around the base, the suctioning and discharging mechanism is configured to suction and discharge the specimen to be processed into the one or more reaction vessels,
wherein the suctioning and discharging mechanism includes a plurality of nozzles that operate independently of each other on the same axis and which are disposed at the different points around the base,
the system further comprising:
a dispensing unit where the specimen to be processed that is accommodated in the specimen container is suctioned and discharged into one of the reaction vessels by the suctioning and discharging mechanism,
wherein the dispensing unit includes a specimen container supply line that includes a belt conveyor to supply the specimen accommodated in the specimen container to the turntable to be suctioned by the suctioning and discharging mechanism;
a hemolyzing unit which hemolyzes the specimen dispensed into the one of the reaction vessels; and a protein precipitating unit which precipitates proteins in the hemolyzed specimen in the one of the reaction vessels, wherein the dispensing unit, the hemolyzing unit, and the protein precipitating unit are arranged along the turntable, wherein the hemolyzing unit includes:
  a specimen container collection line that includes a belt conveyor to carry the specimen container from the turntable to a specimen container collection unit; and
  a hemolyzing solution injector to inject a hemolyzing solution into the one of the reaction vessels, and wherein the protein precipitating unit includes:
  a protein-precipitating solution injector to inject a protein-precipitating solution into the one of the reaction vessels.

2. The specimen processing system according to claim 1, wherein:
  the suctioning and discharging mechanism mixes the specimen to be processed, by repeating suctioning and discharging of the specimen alternately.

3. The specimen processing system according to claim 1, further comprising:
  a nozzle tip that is removably provided on the suctioning and discharging mechanism.

4. The specimen processing system according to claim 3, further executing a plurality of mixing steps with one nozzle tip, for one specimen.

5. The specimen processing system according to claim 1, wherein each of the one or more reaction vessels is an integrated vessel including a filtering section and a collection section to retain a filtrate obtained by the filtering section, where the filtering section and the collection section are removable from each other after filtering.

6. The specimen processing system according to claim 1, wherein a circular path during rotation of the suctioning and discharging mechanism and a circular path during rotation of the turntable which carries reaction vessels intersect substantially at two positions, at the two intersections of which the system conducts specimen dispensing and reaction solution mixing.

7. The specimen processing system according to claim 6, wherein the suctioning and discharging mechanism includes two nozzles that operate independently of each other on the same axis, and wherein the suctioning and discharging mechanism undertakes operations on the reaction vessels positioned at the two intersections relative to the path of the turntable which carries the reaction vessels.

8. The specimen processing system according to claim 1, wherein the hemolyzing unit further includes:
  a tank which holds the hemolyzing solution.

9. The specimen processing system according to claim 1, wherein the protein precipitating unit further includes:
  a tank which holds the protein-precipitating solution.

* * * * *